US010583210B2

(12) United States Patent
Thisgaard et al.

(10) Patent No.: US 10,583,210 B2
(45) Date of Patent: Mar. 10, 2020

(54) AUGER ELECTRON THERAPY FOR GLIOBLASTOMA

(71) Applicants: Syddansk Universitet, Odense M (DK); Region Syddanmark, Vejle (DK)

(72) Inventors: Helge Thisgaard, Middelfart (DK); Bo Halle, Odense Sv (DK); Poul Flemming Høilund-Carlsen, Svendborg (DK); Bjarne Winther Kristensen, Odense C (DK); Charlotte Aaberg-Jessen, Odense S (DK)

(73) Assignees: Syddansk Universitet, Odense M (DK); Region Syddanmark, Vejle (DK)

( * ) Notice: Subject to any disclaimer, the term of this patent is extended or adjusted under 35 U.S.C. 154(b) by 239 days.

(21) Appl. No.: 15/320,113

(22) PCT Filed: Jun. 19, 2015

(86) PCT No.: PCT/EP2015/063823
§ 371 (c)(1),
(2) Date: Dec. 19, 2016

(87) PCT Pub. No.: WO2015/193477
PCT Pub. Date: Dec. 23, 2015

(65) Prior Publication Data
US 2017/0151354 A1 Jun. 1, 2017

(30) Foreign Application Priority Data

Jun. 20, 2014 (EP) .................................... 14173218

(51) Int. Cl.
*A61K 51/04* (2006.01)
*A61K 31/495* (2006.01)
*A61K 51/00* (2006.01)

(52) U.S. Cl.
CPC ........ *A61K 51/0491* (2013.01); *A61K 31/495* (2013.01); *A61K 51/04* (2013.01)

(58) Field of Classification Search
CPC ... A61K 51/0491; A61K 31/495; A61K 51/04
See application file for complete search history.

(56) References Cited

U.S. PATENT DOCUMENTS

| 5,077,034 A | 12/1991 | Kassis et al. | |
| 6,987,108 B2 * | 1/2006 | Ugwu | A61K 9/0019 514/243 |
| 2007/0128108 A1 | 6/2007 | Samnick | |
| 2010/0280494 A1 * | 11/2010 | Matsuura | A61M 25/0021 604/523 |

FOREIGN PATENT DOCUMENTS

WO WO2008/140808 11/2008

OTHER PUBLICATIONS

Morgenroth et al., Targeted endoradiotherapy using nucleotides, Methods 55 (2011) 203-214. (Year: 2011).*
Morgenroth et al., Targeted endoradiotherapy using nucleotides, Methods 55 (2011) 203-214, available online Jul. 18, 2011. (Year: 2011).*
Debiniski et al., Convection-enhanced Delivery for the Treatment of Brain Tumors, Expert Rev Neurother. 2009;9(10):1519-1527. (Year: 2009).*
Friedman et al., Temozolomide and Treatment of Malignant Glioma, Clinical Cancer Research vol. 6, 2585-2597, Jul. 2000. (Year: 2000).*
Aaberg-Jessen, et-al., Invasion of primary glioma-and cell linedevrived spheroids implanted into corticostriatal slice cultures, Int. J. Clin. Exp. Pathol., 6(4):546-560, 2013.
Buchegger, F. et-al., Highly Efficient DNA Incorporation of Intratumourally Injected [125I]lododeoxyuridine Under Thymidine Synthesis Blocking in Human Glioblastoma Xenografts, Int. J. Cancer, 110, 145-149, 2004.
Buonerba, C. et al., A comprehensive outlook on intracerebral therapy of malignant gliomas, Critical Reviews in Oncology/Hematology, 80(1): 54-68, Sep. 1, 2010.
Butkowski, N. et al., Diagnosis and Treatment of Recurrent High-Grade Astrocytoma, Journal of Clinical Oncology, 24(8): 1273-80, Mar. 10, 2006.
Dam, J. et-al., P-025 Fully automated radiosynthesis and formulation of [11C]MeAIB applied for in vivo imaging of glioblastoma, S112 20th International Symposium on Radiopharmaceutical Sciences, J Label Compd Radiopharm, 56; S1-S492, 2013.
De Vries, N. et al., High-grade glioma mouse models and their applicability for preclinical testing, Cancer Treatment Reviews, 35(8): 714-23, 2009.
Kassis, A. et-al., 5-[125I]Iodo-2'-Deoxyuridine in the Radiotherapy of Brain Tumors in Rats, The Journal of Nuclear Medicine 1998; 39:1148-1154.
Lehnert, S. et-al., 125I-Iododeoxyuridine for the Treatment of a Brain Tumor Model: Selection of Conditions for Optimal Effectiveness, The Open Nuclear Medicine Journal, 2011, 3, 19-24.
Mairs, R. et-al., Comparison of different methods of intracerebral administration of radioiododeoxyuridine for glioma therapy using a rat model, British Journal of Cancer (2000) 82 (1), 74-80.

(Continued)

*Primary Examiner* — Michael G. Hartley
*Assistant Examiner* — Nabila G Ebrahim
(74) *Attorney, Agent, or Firm* — Julie K. Staple; Dinsmore & Shohl LLP

(57) ABSTRACT

A method is provided for treating or ameliorating a high-grade glioma in a patient, which method comprises intracerebral administering of a radioactive agent characterized by a short-range cytotoxic ionizing radiation by convection-enhanced delivery. Further, a radioactive agent characterized by a short-range cytotoxic ionizing radiation is provided for use in treating or ameliorating a high-grade glioma, where the agent is administered by intracerebral convection-enhanced delivery.

8 Claims, 19 Drawing Sheets

(56) References Cited

OTHER PUBLICATIONS

Neshasteh-Riz, A. et-al., Incorporation of iododeoxyuridine in multicellular glioma spheroids: implications for DNA-targeted radiotherapy using Auger electron emitters, British Journal of Cancer, 75(4), 493-499, 1997.

O'Donoghue, et al., Targeted radiotherapy using Auger electron emitters targeted radiotherapy using Auger electron emitters, Phys. Med. Biol., pp. 1973-1992, Jan. 1, 1996.

Rousseau, J. et-al., Intracerebral delivery of 5-iodo-2'-deoxyuridine in combination with synchrotron stereotactic radiation for the therapy of the F98 glioma, Journal of Synchrotron Radiation, 2009; vol. 16; 573-581.

Ryken, T. et al., Ongoing Clinical Trials, Neuro-Oncology, 13(Suppl 3): iii85-iii91, Oct. 21, 2011.

Snyder, L. et-al., OT-01. Improving Low-grade glioma extent of resection: Intraoperative confocal microscopy enables visualization of 5-aminolevulinic acid fluorescence, Neuro-Oncology 13: iii85-iii91, 2011.

Wolff, J. et al., High dose methotrexate for pediatric high grade glioma: results of the HIT-GBM-D Pilot study, Journal of Neuro-Oncology, 102(3): 433-442, Aug. 8, 2010.

Yang, W. et al., Convection enhanced delivery of boronated EGF as a molecular targeting agent for neutron capture therapy of brain tumors, Journal of Neuro-Oncology, 95(3): 355-65, Jul. 9, 2009.

Yokosawa, M. et-al., Convection-Enhanced Delivery of a Synthetic Retinoid Am80, Loaded into Polymeric Micelles, Prolongs the Survival of Rats Bearing Intracranial Glioblastoma Xenografts, Tohoku J. Exp. Med., 2010, 221, 257-264.

European Search Report for Application No. 14173218.0-1453.

* cited by examiner

Figure 2, ctd.
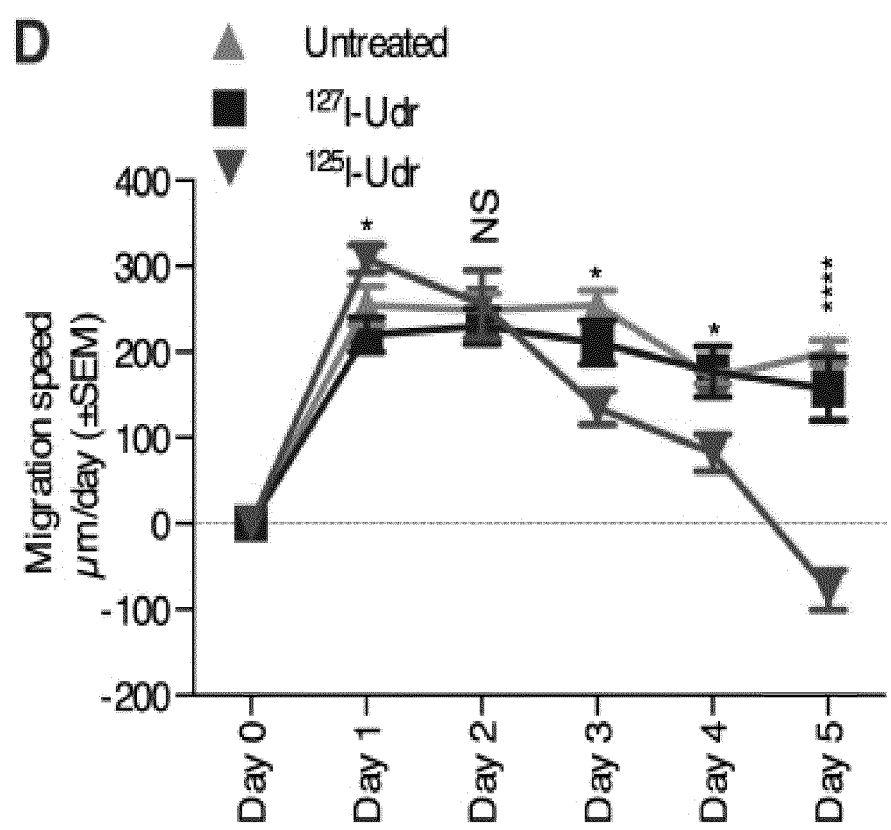

Figure 7, ctd
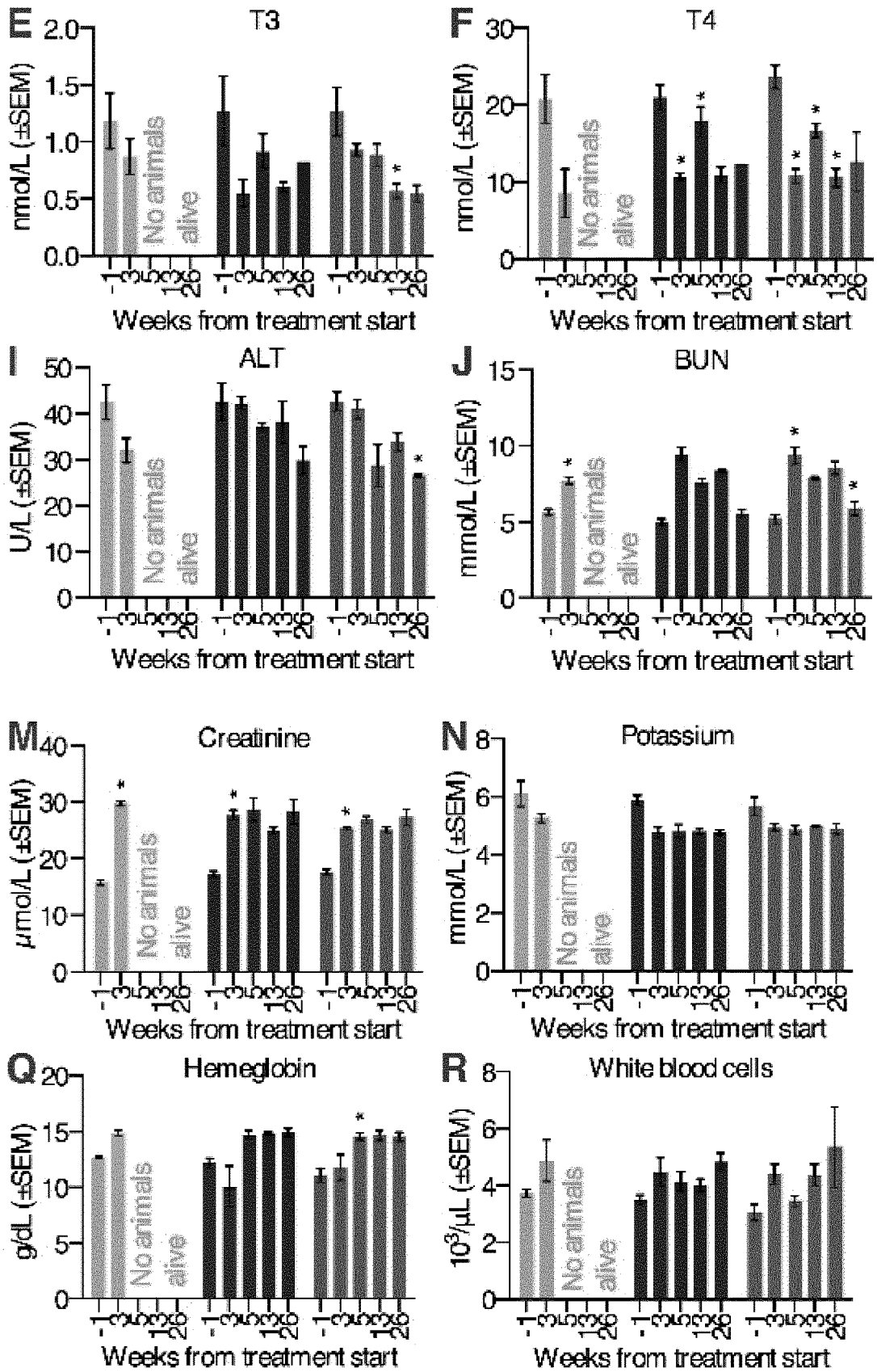

Figure 7, ctd
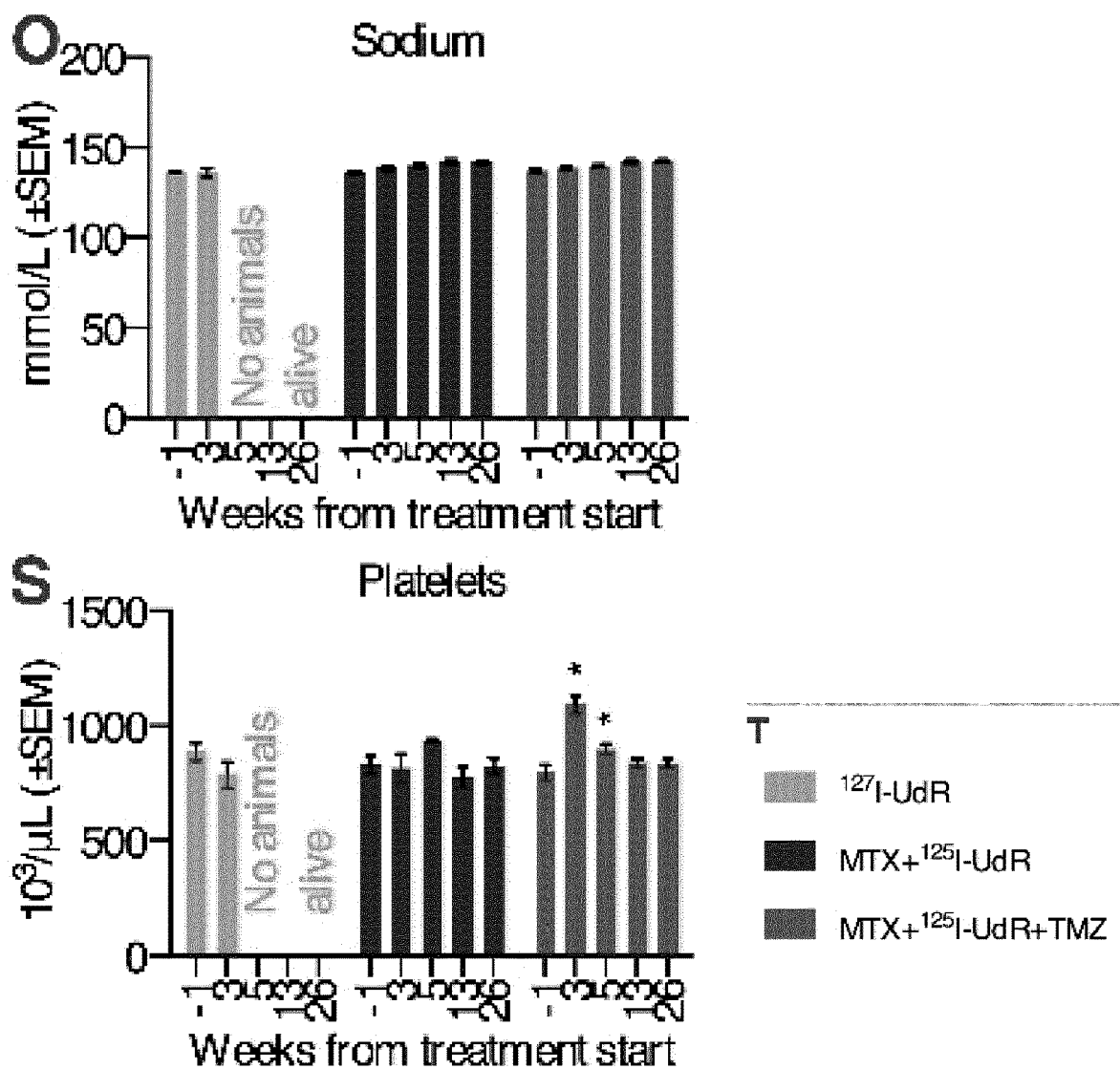

Figure 13, ctd
B
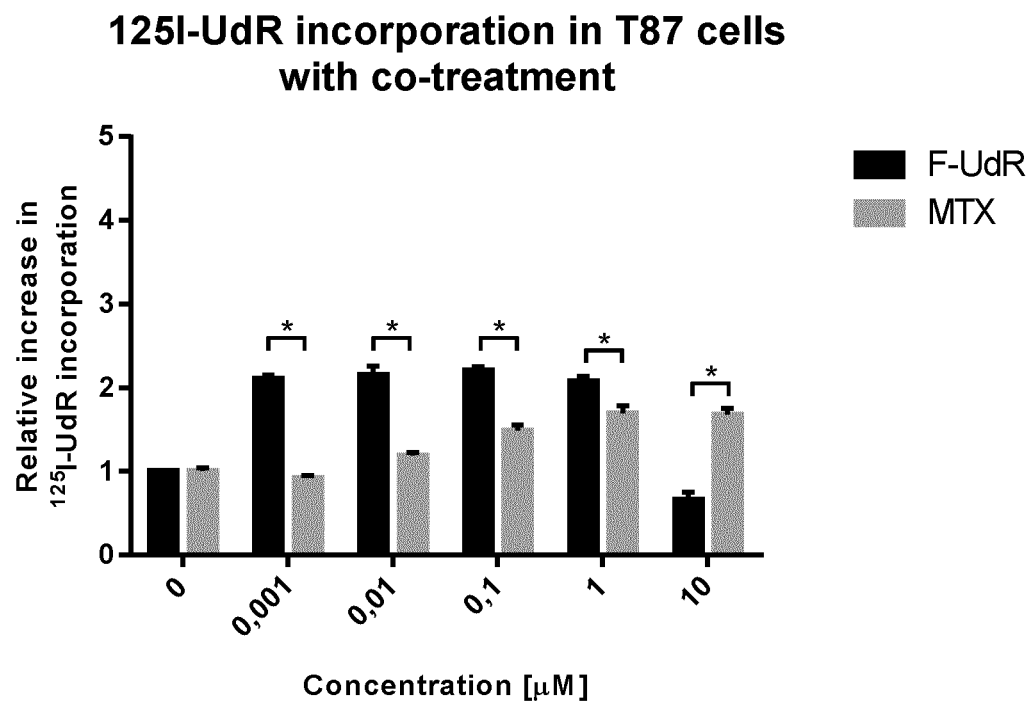
C
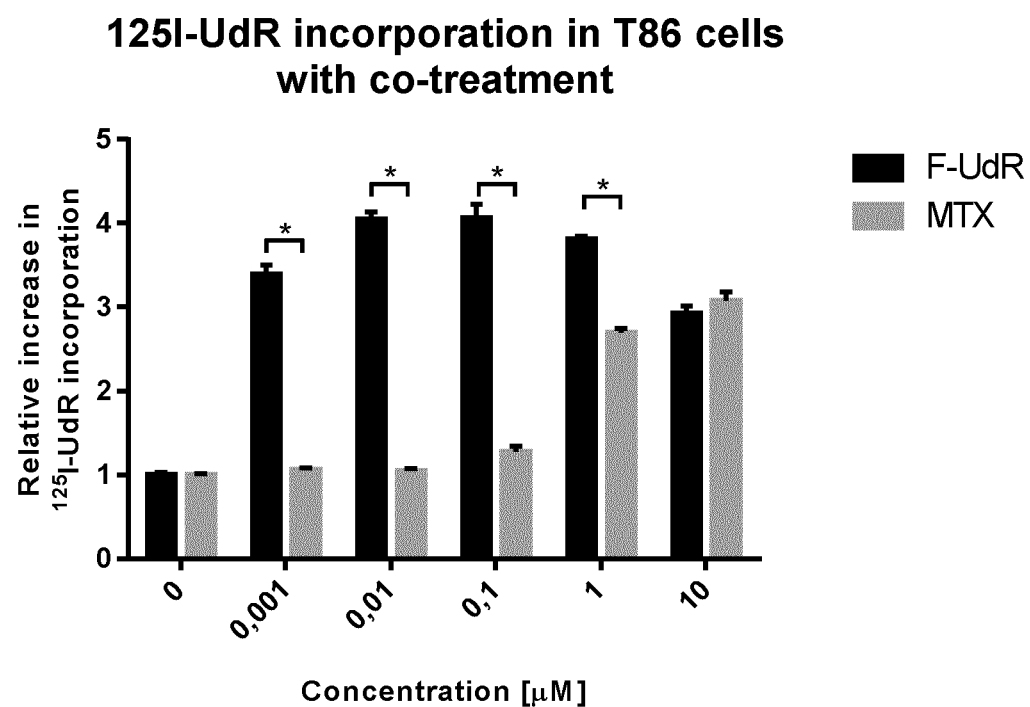

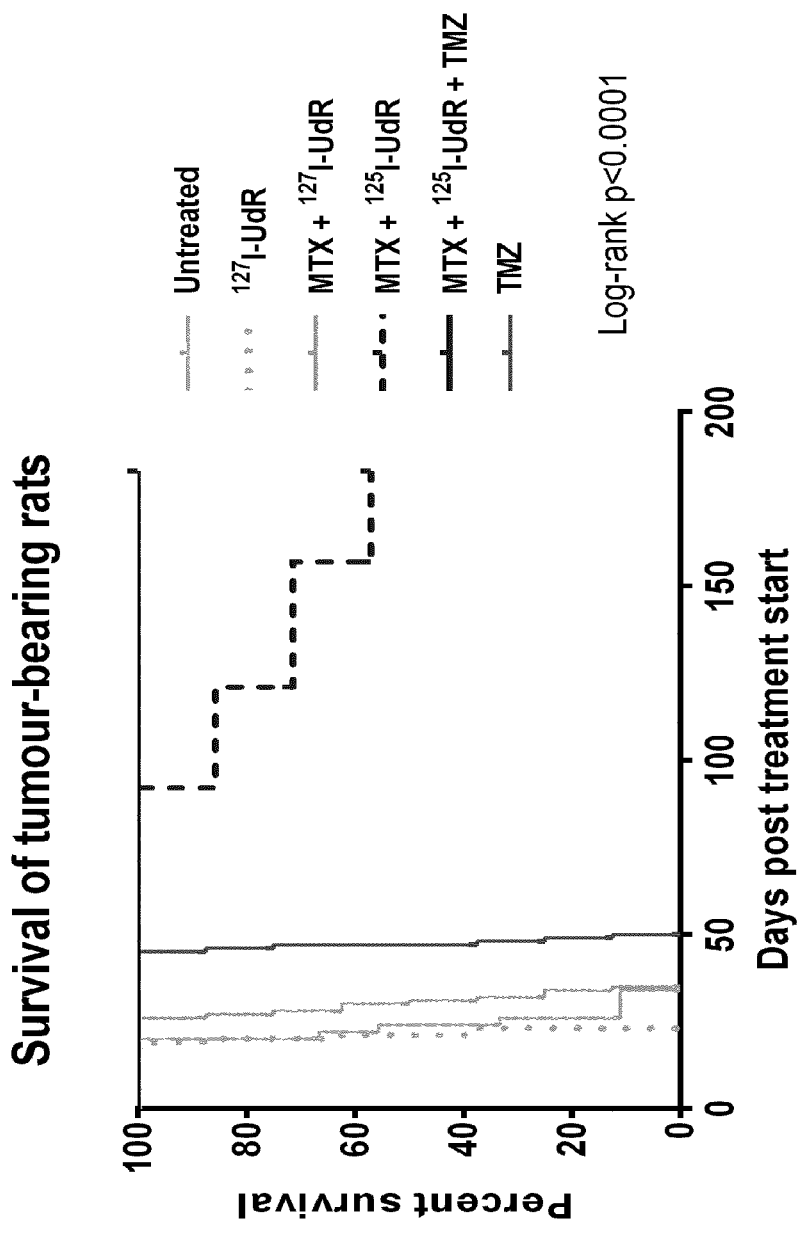
Figure 14, ctd
B

AUGER ELECTRON THERAPY FOR GLIOBLASTOMA

FIELD OF INVENTION

The present invention relates to the use of auger electron therapy for treatment of glioblastoma.

BACKGROUND OF INVENTION

In locally advanced tumors, such as brain tumors, surgery may be used for gross excision, but the surgeon cannot eliminate individual tumor cells, microscopic tumor processes, or tumor-associated vasculature from the normal tissue surrounding the tumor excision site. It is often critical to minimize the volume of surrounding tissue that is excised in such operations. For example, normal brain functions may be severely compromised as a result of tissue loss. Thus, in such cases surgery is often accompanied by radiation therapy and/or chemotherapy in an attempt to kill cancerous cells remaining in the surrounding brain tissue. The chemotherapy may be delivered to the residual tumor cells by a localized or systemic route of administration. By limiting the extent of surgical excision, and relying upon the adjunctive treatments to eliminate the residual cancer cells, the function of an organ may be preserved.

Conventional radiation therapy, using ionizing radiation beams (X-rays, gamma rays, or high energy beta particles), while well-established as an anticancer treatment modality, is not curative in the majority of patients with advanced brain tumors.

Glioblastomas are the most common and malignant type of primary brain cancer and glioblastoma always recur after standard treatment consisting of surgery, radiation and chemotherapy. The overall median survival is only approximately 3 months following surgical resection, 8 months with adjuvant external radiotherapy and 14 months with concurrent and adjuvant alkylating chemotherapy using temozolomide (TMZ). Due to their invasive nature, glioblastomas are non-curable by surgery and side effects as well as poor blood-brain-barrier (BBB) penetration are dose-limiting for conventional chemo- and radiotherapy. Sub-lethal doses may favor escape of cancer cells from therapy and cause resistance development.

Being highly chemo- and radioresistant in experimental studies, a subpopulation of the most resilient cancer cells is most likely a very important part of this therapeutic resistance. These cells are often referred to as cancer cells with stem-like properties or cancer stem cells (CSCs). Cancer stem cells have been described in other cancers, such as lung cancer, malignant melanoma and brain tumors. They appear to replenish the pool of cancer cells, to be highly metastatic and particularly resistant against conventional chemo- and radiotherapies. It is suspected that the cancer stem cells may escape primary therapy due to the limited doses that can be applied.

In most tumors, cancer stem cells comprise no more than 1% of the total tumor cell population, and yet these cells are supposedly responsible for maintaining the growth of the entire tumor by virtue of their capacity for self-renewal and extended proliferation. When transplanted into immuno-compromized rodents, only the cancer stem cells are tumor initiating. In fact, cancer stem cells can recapitulate the distinctive microscopic architectural patterns characteristic of the original human tumor from which the cells were isolated. Cancer stem cells are believed to proliferate rather slowly, and they represent only a small proportion of the cycling/dividing cells within a tumor (as observed at a given time). Cancer stem cells give rise to a more rapidly proliferating subpopulation of cancer cells, known as transit-amplifying or progenitor cancer cells, which comprise the vast majority of cycling/dividing cells observed in the tumor. The transit-amplifying cancer cells and cancer stem cells differ in multiple ways. Unlike the cancer stem cells, transit-amplifying cancer cells lack the capacity for self-renewal and undergo only a limited number of cell divisions before completely losing their proliferative capability. In contrast to cancer stem cells, transit-amplifying cancer cells cannot efficiently form progressive tumors when transplanted into immuno-compromised rodents. Transit-amplifying cancer cells give rise to yet another subpopulation of cancer cells that cannot divide. These post-mitotic cancer cells comprise the majority of cells in many solid tumors. Thus, solid tumors are comprised of at least three distinct subpopulations of malignant cells, each endowed with a different capacity for cell division and continuing growth. Indeed, the vast majority of cells in most solid tumors cannot support progressive tumor growth or lead to tumor recurrence after an initial remission or response to treatment.

The tumor-shrinking and/or tumor-inhibiting activities of ionizing radiation and currently used anticancer drugs are believed to involve direct effects on the transit-amplifying cancer cells, and in many cases the blood vessels that supply tumors. None of these two major treatment modalities are capable of eradicating locally advanced solid tumors or preventing the recurrence of locally advanced solid tumors without causing severe damage to the tissues in which the cancer originated; and similarly, none of these major treatment modalities is capable of producing long term remissions of most types of locally advanced solid tumors, even when used in combination. Ionizing radiation and currently used drugs usually provide only a short term effect on tumor growth.

Cancer stem cells can therefore be seen as the root of the tumor, and elimination of transit-amplifying and post-mitotic cancer cell subpopulations resembles weed whacking, because it is invariably associated with re-growth of the tumor. The elimination of cancer stem cells therefore appears to be a prerequisite for curing advanced solid tumors. Consequently, there is a need for identifying targeted agents that can selectively kill the cancer stem cells while sparing normal stem cells.

Cancer stem cells have been isolated and characterized in patients with many types of malignancies, including glioblastoma multiforme. Because cancer stem cells are responsible for the maintenance of glioblastoma multiforme tumors, this subpopulation of cells must be eliminated to prevent tumor recurrence following treatment, and to achieve long term survival.

However, eradicating brain cancer stem cells is a great challenge. There are several problems associated with brain cancer treatment. First, it appears that solid tumors, such as glioblastoma multiforme, are much more genetically and metabolically heterogeneous than previously anticipated. Solid tumors, as well as the cancer stem cells that drive their growth, appear to be genetically and metabolically heterogeneous despite a common organ or tissue of origin, and despite very similar appearances under the microscope. This is especially true of malignant gliomas, which arise in the central nervous system. In view of the genetic/metabolic heterogeneity of solid tumors, biochemical targeting (i.e. the search for agents that specifically target the stem cells in each type of tumor) is a daunting challenge. Moreover, brain cancer stem cells and other types of cancer stem cells are inherently resistant to chemotherapeutic agents, in part due to elevated expression of drug efflux transport proteins. Also, brain cancer stem cells are resistant to ionizing radiation due to the preferential induction of DNA damage-response genes that repair DNA damage caused by radiation. For example, glioma stem cells promote radioresistance by preferential activation of the DNA damage response. Finally, brain cancer stem cells are believed to proliferate more slowly than other cell populations within the tumor thereby making them less susceptible to the toxic effects of cell cycle active agents and ionizing radiation. Cancer stem cells are also believed to proliferate/cycle at a slower rate than their immediate progeny, the transit-amplifying cancer cells.

A unique cell killing mechanism that has garnered considerable interest is the release of Auger electrons. These electrons are emitted by radionuclides that decay by electron capture and internal conversion. Auger electrons have energies even lower than the energy of the beta particle emitted by tritium. This effect is amplified, because some Auger emitters release multiple electrons with each nuclear transformation. The low energy of the Auger electrons results in extremely short particle path lengths within tissues, which is highly desirable, because it minimizes collateral damage. One molecular entity incorporating $^{125}$Iodine is [$^{125}$I]-iodouridine-deoxyriboside ($^{125}$I-UdR), a thymidine analog. $^{125}$I-UdR is recognized by DNA polymerases as a normal thymidine metabolite, and thus is incorporated into the chromosomes at times of DNA synthesis. Once incorporated into the DNA, the Auger electrons, with their very short range (often less than 10 nm), have access to the chemical backbone of the DNA duplex. When the $^{125}$Iodine atom disintegrates, Auger electrons have the potential to cause severe damage to chromosomes with minimal effect on cells in the immediate vicinity of the target cell.

Despite the recognition that $^{125}$I-UdR has a unique cell killing capability, and despite many years of research aimed at exploiting this mechanism of action, including the concept of directly introducing $^{125}$I-UdR into tumors (cf. Mairs et al, Br J Cancer. 2000 January; 82(1):74-80), these agents have not been successfully applied to the treatment of cancer. The delivery of $^{125}$I-UdR and related agents to solid tumors, using systemic or local administration, has proven to be extremely challenging.

Thus, new therapeutic strategies are called for that are able to eliminate cancer stem cells in treatment of advanced brain tumors.

SUMMARY OF INVENTION

The present invention relates to the treatment and/or amelioration of high-grade gliomas (WHO grade III-IV) by administration of a radioactive agent characterized by a short-range cytotoxic ionizing radiation. The radioactive agent is preferably administered by intracerebral convection-enhanced delivery.

Thus, in one aspect, the present invention relates to a radioactive agent characterized by a short-range cytotoxic ionizing radiation for use in treating or ameliorating a high-grade glioma (WHO grade III-IV). The radioactive agent is preferably administered by intracerebral convection-enhanced delivery. Accordingly, in one aspect, the present invention relates to a radioactive agent characterized by a short-range cytotoxic ionizing radiation for use in treating or ameliorating a high-grade glioma (WHO grade III-IV), wherein the agent is administered by intracerebral convection-enhanced delivery.

In another aspect, a composition is provided comprising a radioactive agent characterized by a short-range cytotoxic ionizing radiation, wherein the composition is prepared for administration by intracerebral convection-enhanced delivery. Thus, the composition is in a preferred embodiment a liquid solution of isotonic saline buffer or PBS buffer, optionally comprising ethanol.

In a further aspect, a method is provided of treating or ameliorating a high-grade glioma comprising administering a radioactive agent characterized by a short-range cytotoxic ionizing radiation to a person in need thereof. The radioactive agent is preferably administered by convection-enhanced delivery. Thus in one aspect, a method is provided of treating or ameliorating a high-grade glioma in a patient comprising intracerebral administering of a radioactive agent characterized by a short-range cytotoxic ionizing radiation by convection-enhanced delivery to a person in need thereof.

In an additional aspect, a kit-of-parts is provided comprising a combined preparation comprising or containing a radioactive agent characterized by a short-range cytotoxic ionizing radiation and
a) at least one additional therapeutic agent and/or
b) at least one further agent,
for the simultaneous, separate or sequential administration for treating or ameliorating a high-grade glioma.

In one aspect, a kit-of-parts is provided which comprises a combined preparation comprising or containing 1) a radioactive agent characterized by a short-range cytotoxic ionizing radiation and 2) at least one further therapeutic agent and/or at least one additional chemotherapeutic agent, for the simultaneous, separate or sequential administration for treating or ameliorating a high-grade glioma.

In a fourth aspect, the present invention relates to a radioactive agent characterized by a short-range cytotoxic ionizing radiation for use in the manufacture of a medicament for the treatment or amelioration of a high-grade glioma, wherein said radioactive agent is administered by convection-enhanced delivery.

A radioactive agent characterized by a short-range cytotoxic ionizing radiation is also in one aspect provided for treatment or amelioration of a high-grade glioma. The radioactive agent is preferably administered by convection-enhanced delivery.

UdR. Migration was significantly inhibited from day 3 in the $^{125}$I-UdR exposed spheroids compared to both untreated and $^{127}$I-UdR exposed spheroids. (D) As with C but with T78 spheroids. NS: p>0.05; *: p<0.05; *: p<0.001; **: p<0.0001.

Figure 3:
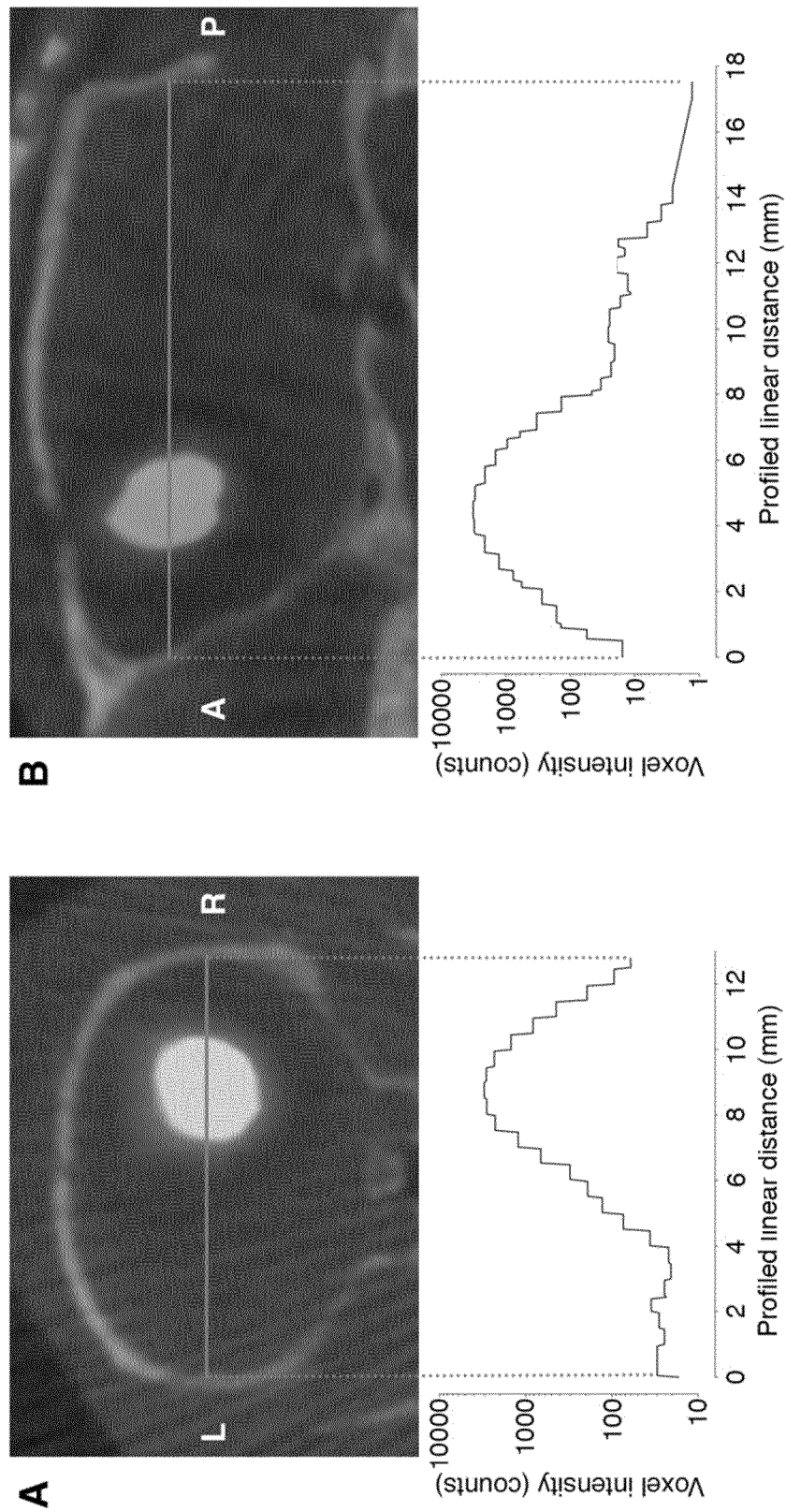

FIG. 3: SPECT/CT scan of MTX+$^{125}$I-UdR treated rat performed on the last day of $^{125}$I-UdR infusion. (A) Axial view showing a decline in $^{125}$I activity concentration in the contralateral hemisphere compared to the isocenter of delivery in the right hemisphere. (B) Sagittal view showing a decline in $^{125}$I activity concentration towards the caudal part of the brain compared to the frontal isocenter of delivery.

Figure 4:
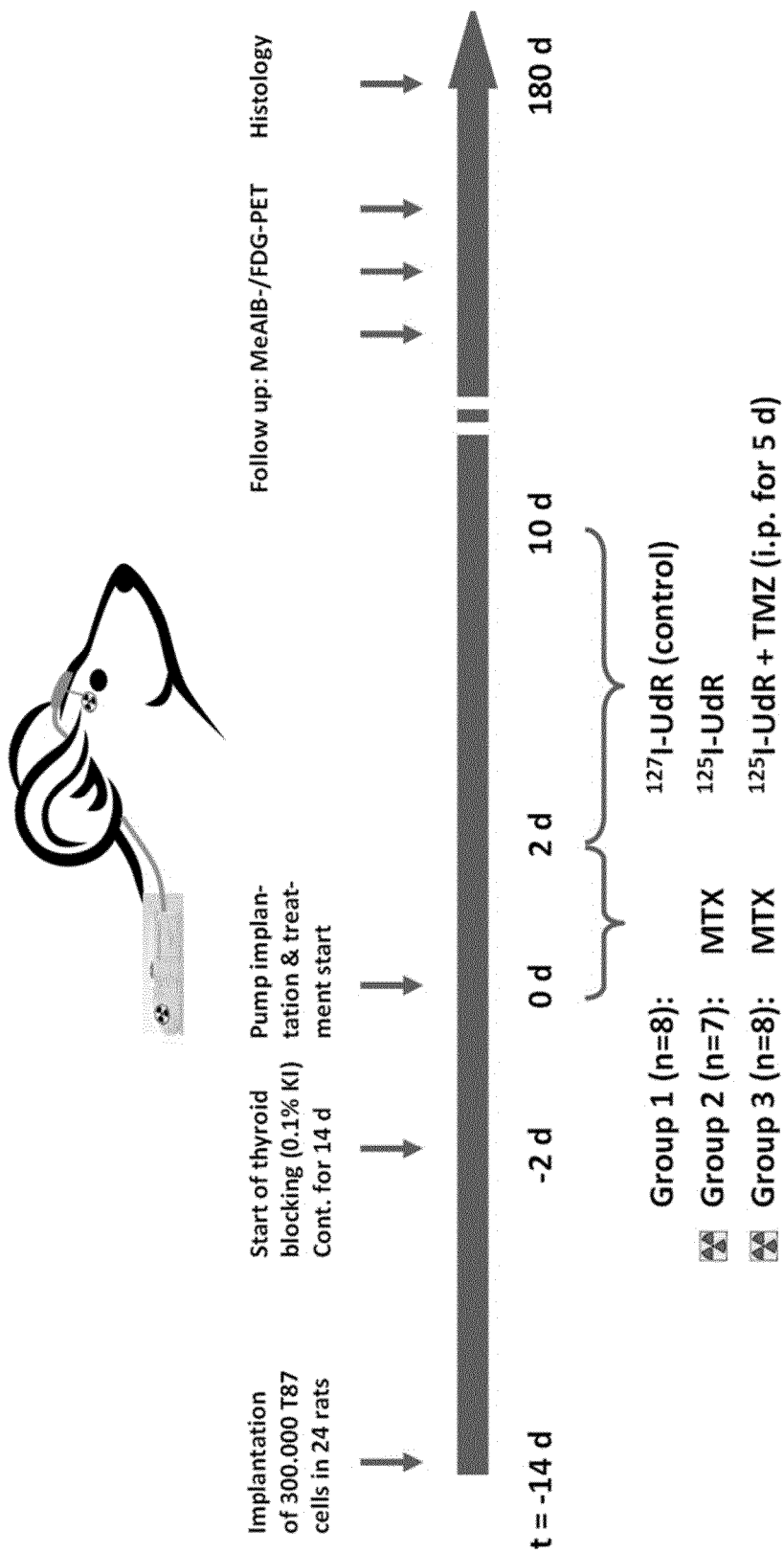

FIG. 4: Schematic view of the in vivo study in human GBM-bearing athymic nude rats. Upon tumor formation (14 days post tumor cell implantation) rats had a micro infusion pump implanted with a catheter going directly into the brain tumor. After 2 days infusion of saline or MTX the pump reservoirs were emptied and refilled with either $^{127}$I-UdR (placebo) or $^{125}$I-UdR. These compounds were then infused as a single dose regimen for 8 consecutive days. In one of the treatment arms concomitant TMZ was given intraperitoneally. Tumor response was followed by PET scans using [$^{11}$C]MeAIB. At the end of the study period all brains were examined histologically.

Figure 5:
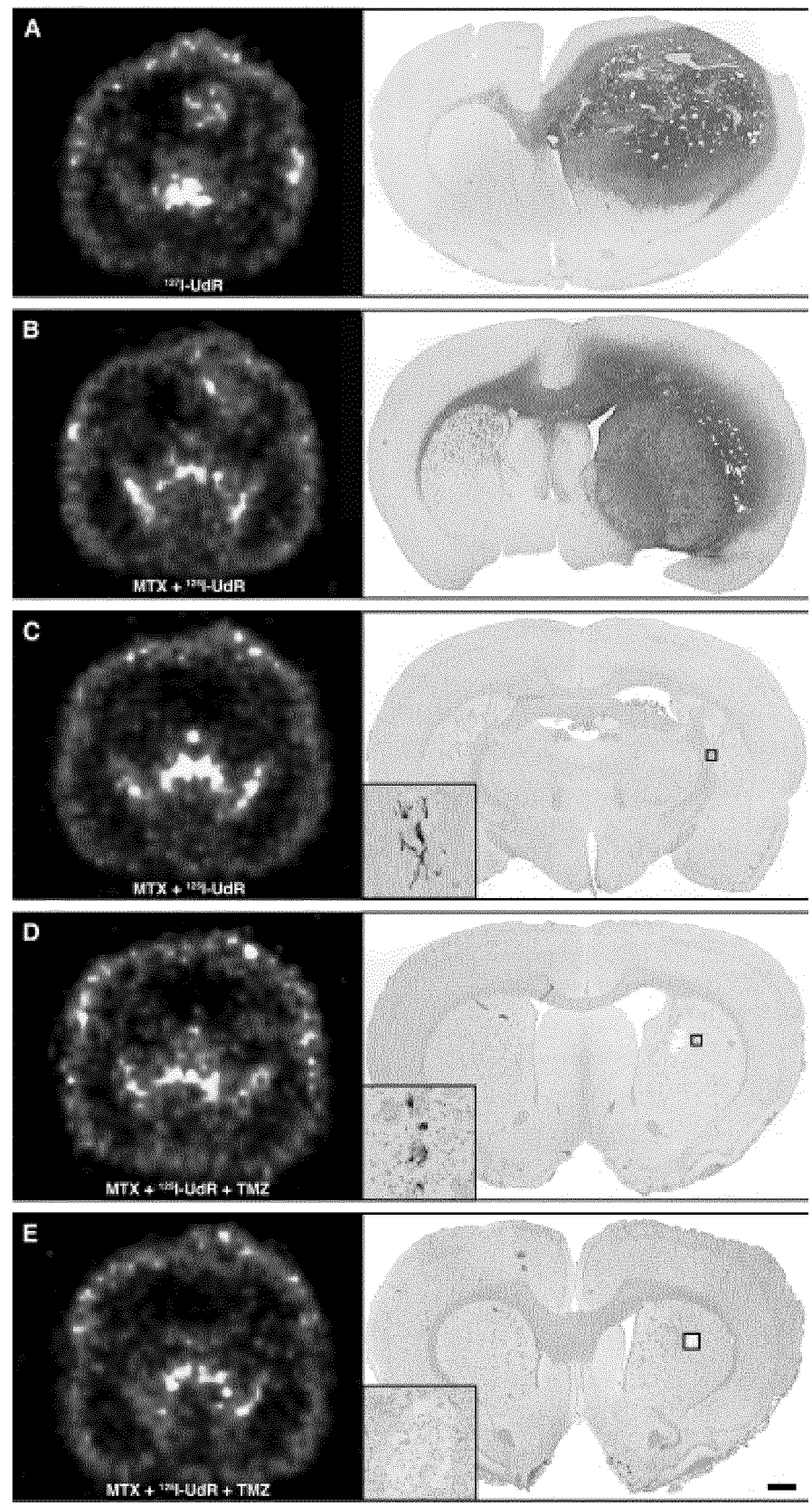

FIG. 5: [$^{11}$C]MeAIB PET images and corresponding histological anti-human vimentin stained coronal brain sections. (A) PET image of a $^{127}$I-UdR treated rat 21 days after treatment start showing a grossly big tumor, confirmed by histology 2 days later. (B) PET image of a MTX+$^{125}$I-UdR treated rat 91 days after treatment start showing a grossly big tumor confirmed by histology the following day. (C) PET image of a MTX+$^{125}$I-UdR treated rat 178 days after treatment start with no PET visualizable tumor. Histology two days later showed an empty tumor bed with a few GBM cells located in close vicinity (black box). (E) PET image of a MTX+$^{125}$I-UdR+TMZ treated rat 178 days after treatment start with no PET visualizable tumor. Histology two days later showed an empty tumor bed with a few GBM cells located in close vicinity (black box). (F) PET image of a MTX+$^{125}$I-UdR+TMZ treated rat 178 days after treatment start with no PET visualizable tumor. Histology two days later showed an empty tumor bed (black box) and no identifiable GBM cells at all.

Figure 6:
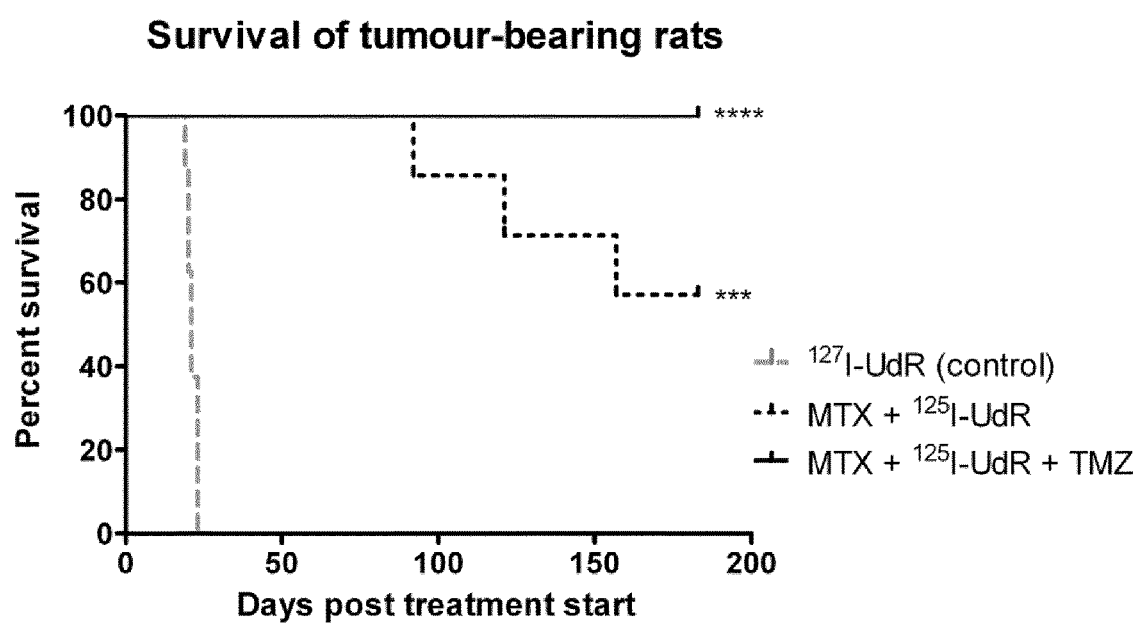

FIG. 6: Kaplan-Meier survival curve of human GBM-bearing athymic nude rats treated with either CED of the non-radioactive $^{127}$I-UdR (group 1), CED of MTX+$^{125}$I-UdR (group 2) or CED of MTX+$^{125}$I-UdR+concomitant systemic TMZ chemotherapy (group 3). *: p<0.001; **: p<0.0001.

Figure 7:
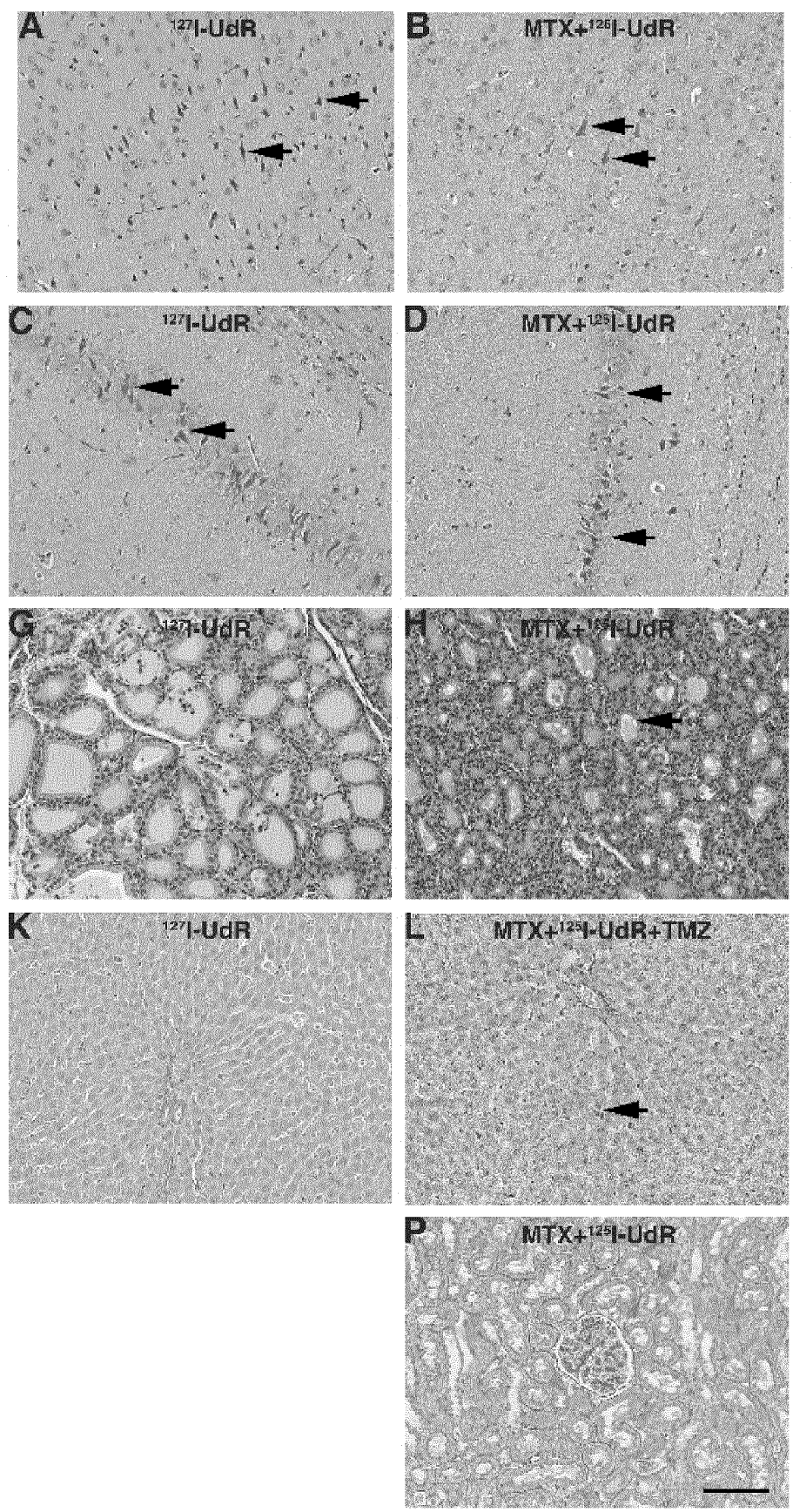

FIG. 7: No signs of dose-limiting adverse effects of MTX, $^{125}$I-UdR and TMZ treatment. (A-D) HE stained brain sections from $^{127}$I-UdR and MTX+$^{125}$I-UdR treated rats. Some black neurons (black arrows) were present in the cortex (A, B) and the hippocampus (C, D). (E) Total T3 and (F) total T4 thyroid hormone blood levels. (G) HE stained section of thyroid gland showing normofollicular architecture in a $^{127}$I-UdR treated rat. (H) Similar HE stained section from a MTX+$^{125}$I-UdR treated rat showing microfollicular architecture and colloids with scalloped margins (black arrow). (I) ALT and (J) BUN blood levels. (K) PAS-diastase staining of a liver section from a $^{127}$I-UdR treated rat showing normal liver architecture and no signs of hepatocyte necrosis, haemorrhage or inflammation. (L) Similar PAS-diastase staining from a MTX+$^{125}$I-UdR treated rat, showing a few necrotic hepatocytes (black arrow). The liver architecture was normal and no haemorrhages were seen. (M) Creatinine, (N) potassium and (O) sodium blood levels. (P) PAS staining of kidney from a MTX+$^{125}$I-UdR treated rat showing no signs of tubular damage or interstitial fibrosis. (Q) Hemoglobin, (R) white blood cell and (S) platelet levels. *: p<0.05.

Figure 8:
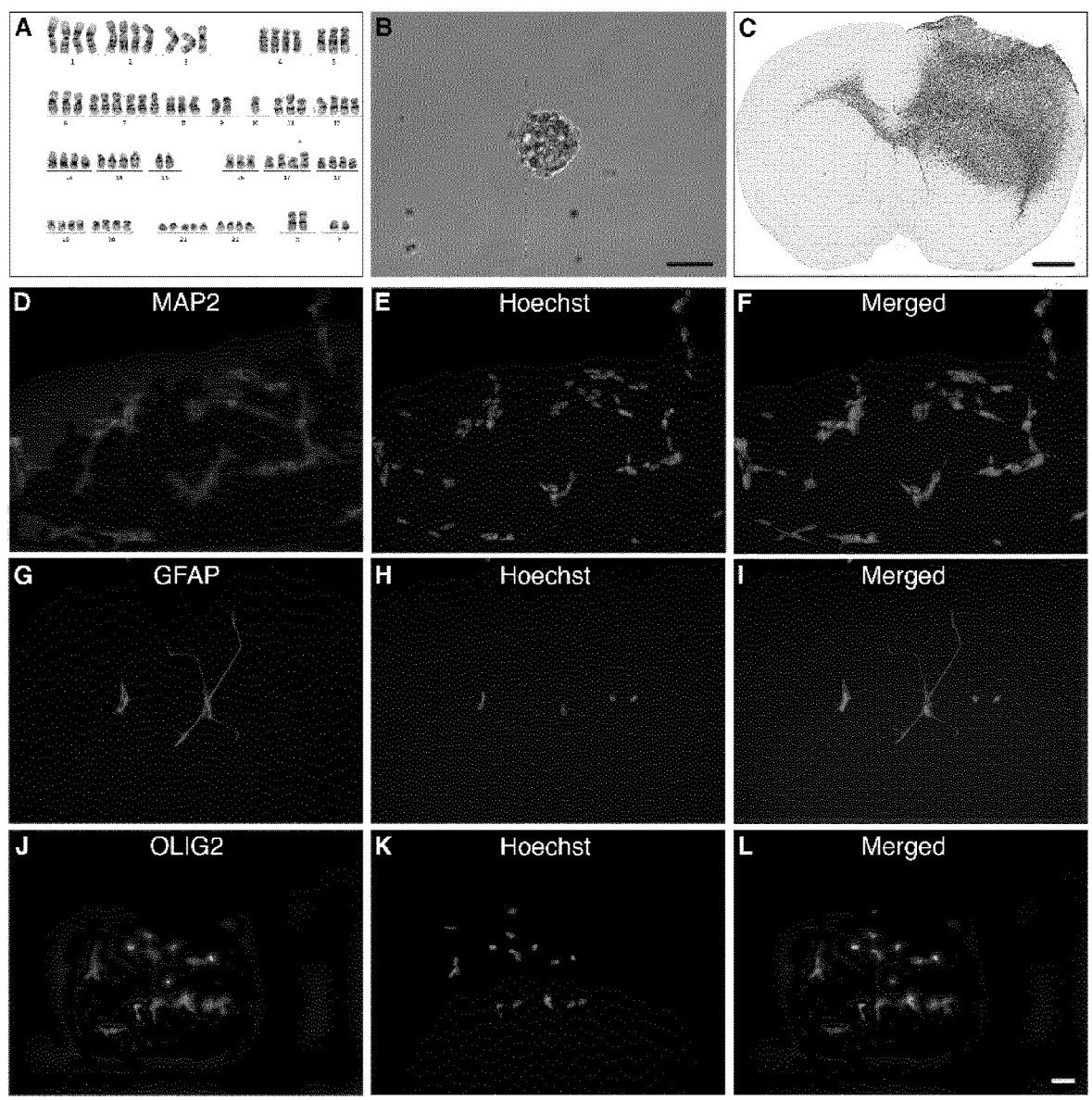

FIG. 8: Characterization of the glioblastoma spheroid cultures used in the present study, exemplified by the T87 glioblastoma spheroid culture. (A) The T87 karyotype showed gain of chromosome 7 and loss of chromosome 10, typical for glioblastomas. (B) Dissociated T87 cells formed spheroids at clonal density when cultured in serum-free medium. (C) In vivo xenografting of 300,000 T87 single cells into the right striatum of immunodeficient mice produced highly invasive tumors. The tumors were identified by immunohistochemical anti-human vimentin staining of paraffin embedded coronal sections of the brains. (D-L) Differentiation assay with the neuronal marker MAP2, the astrocytic marker GFAP and the oligodendrocyte marker OLIG2. Upon culturering in serum-containing medium T87 cells had the ability to differentiate, identified by the expression of (D-F) MAP2, (G-I) GFAP and (J-L) OLIG2. Scale bar 100 μm (B), 2 mm (C), 50 μm (D-L).

Figure 9:
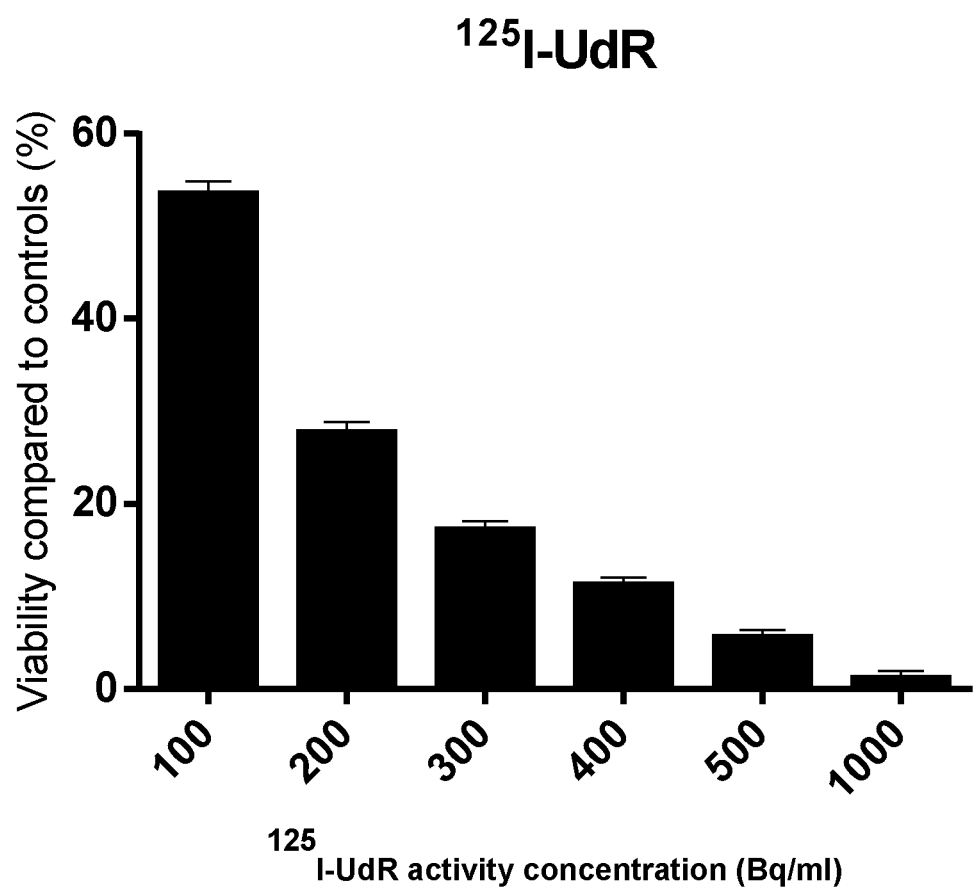

FIG. 9: $^{125}$I-UdR treatment of T87 GBM cells in vitro. Cell viability of T87 glioblastoma cells after exposure to increasing activity concentrations of $^{125}$I-UdR for 7 days. The viability is shown in percent compared to non-treated control cells. The experiment was performed three times with κ wells of each concentration and the final result and error bars representing SEM was calculated on the basis of all 15 values. IC$_{50}$ was calculated to 109 Bq/mL (99-120 Bq/mL) by non-linear regression analysis. The therapeutic potential of $^{125}$I-UdR is demonstrated as a negative correlation between cell viability and increasing activity dose.

Figure 10:
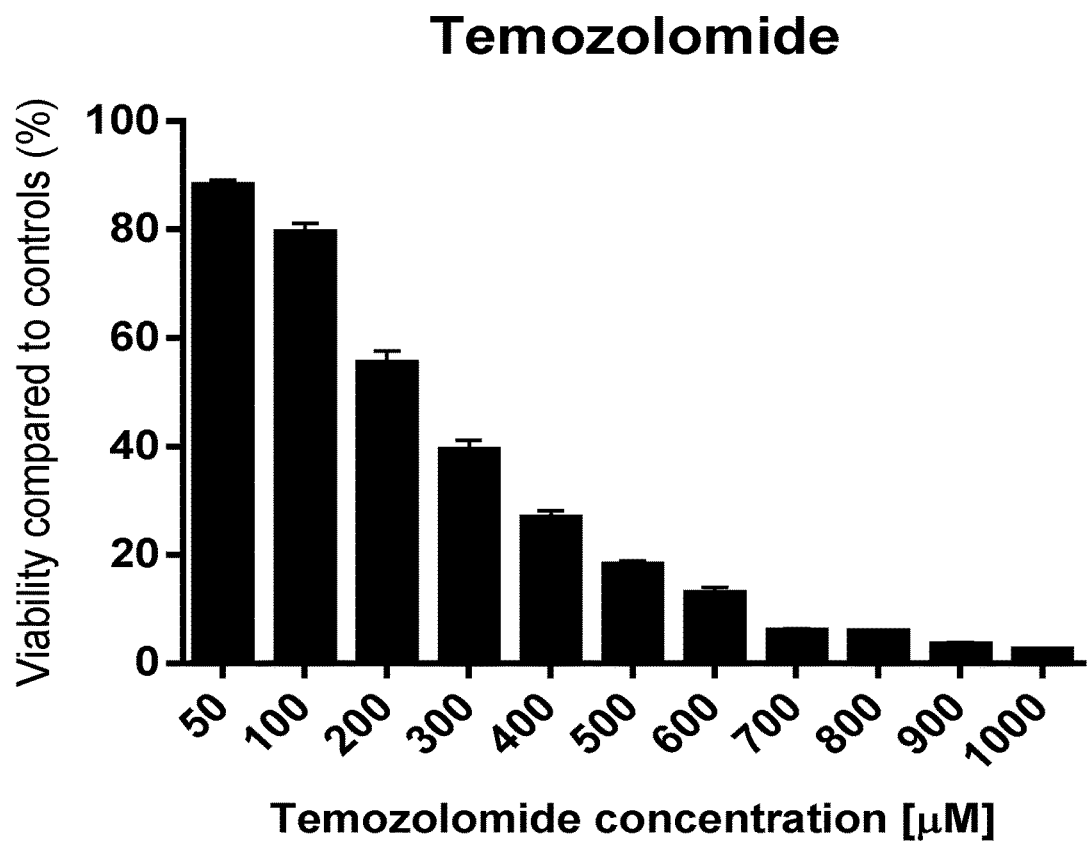

FIG. 10: Temozolomide treatment of T87 GBM cells in vitro.
Cell viability of T87 cells after exposure to increasing concentrations of Temozolomide (TMZ) for 7 days. The viability is shown in percent compared to non-treated control cells. IC$_{50}$ was calculated to 206 μM (198-214 μM) by non-linear regression analysis. The experiment was performed three times with κ wells of each concentration and the final result and error bars representing SEM was calculated on the basis of all 15 values. The therapeutic potential of TMZ is demonstrated as a negative correlation between cell viability and increasing dose.

Figure 11:
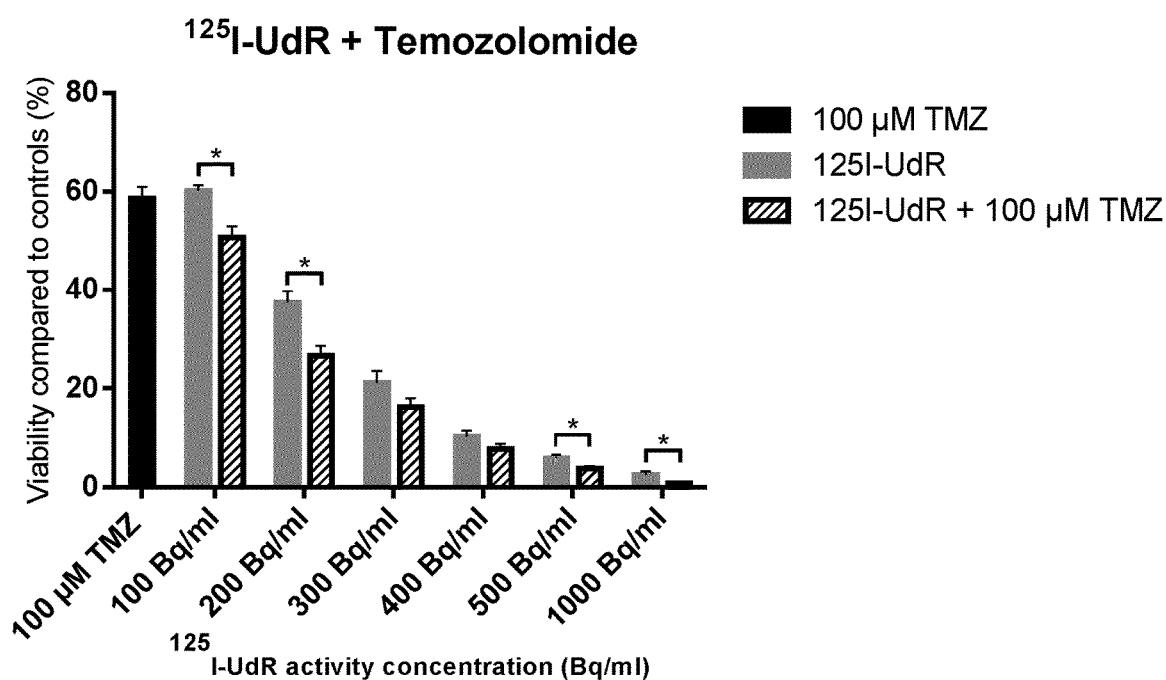

FIG. 11: Combined $^{125}$I-UdR and Temozolomide treatment of T87 GBM cells in vitro. Cell viability of T87 cells after exposure to increasing activity concentrations of $^{125}$I-UdR with or without additional 100 μM (approx. IC$_{50}$) TMZ for 7 days. The viability is shown in percent compared to non-treated control cells. No sign of synergy between $^{125}$I-UdR and TMZ was observed. However a significant higher therapeutic effect was observed when the cells were treated with both $^{125}$I-UdR and TMZ compared to cells treated with $^{125}$IUdR alone.

Figure 12:
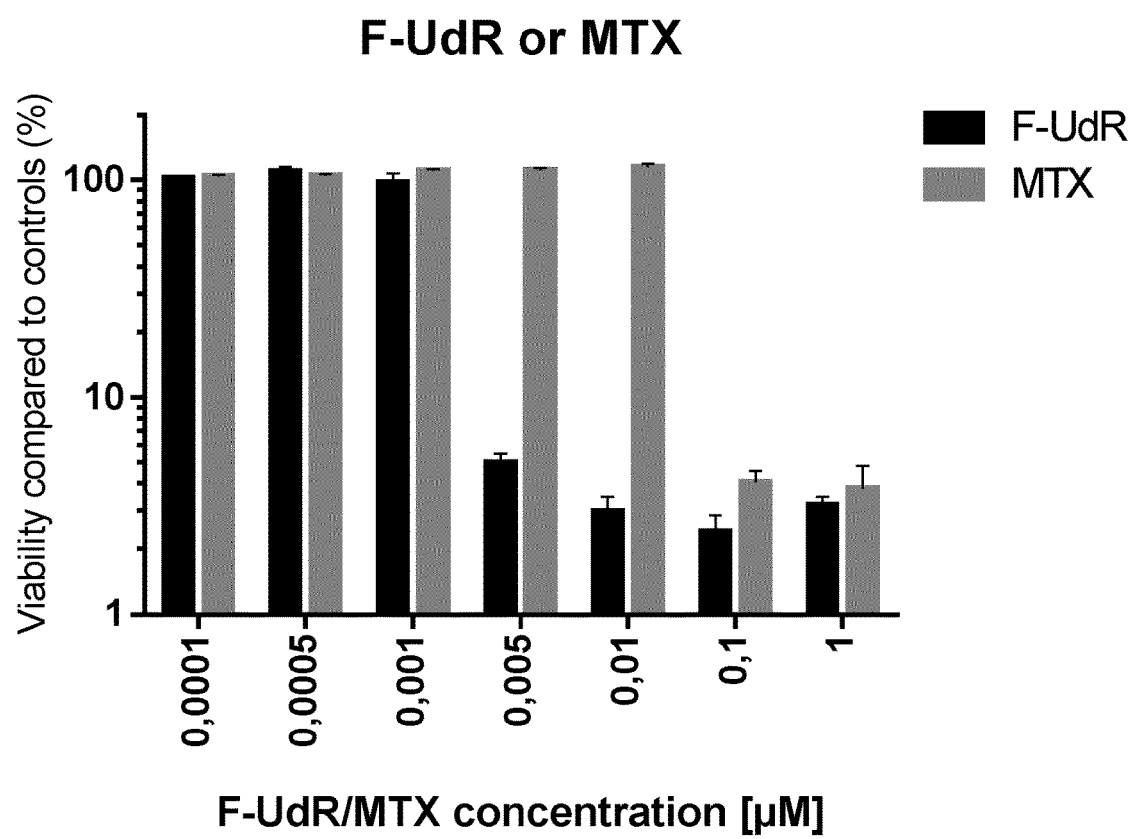

FIG. 12: Methotrexate or 5-Fluoro-2'-deoxyuridine treatment of T87 GBM cells in vitro.
Cell viability of T87 cells after exposure to increasing concentrations of either methotrexate (MTX) or 5-Fluoro-2'-deoxyuridine (F-UdR) for 7 days. The viability is shown in percent compared to non-treated control cells. The experiment was performed three times with 5 wells of each concentration and the final result and error bars representing SEM was calculated on the basis of all 15 values. All cells were viable when exposed to 50.01 μM MTX and 50.001 μM F-UdR indicating a stronger killing effect of F-UdR.

Figure 13:
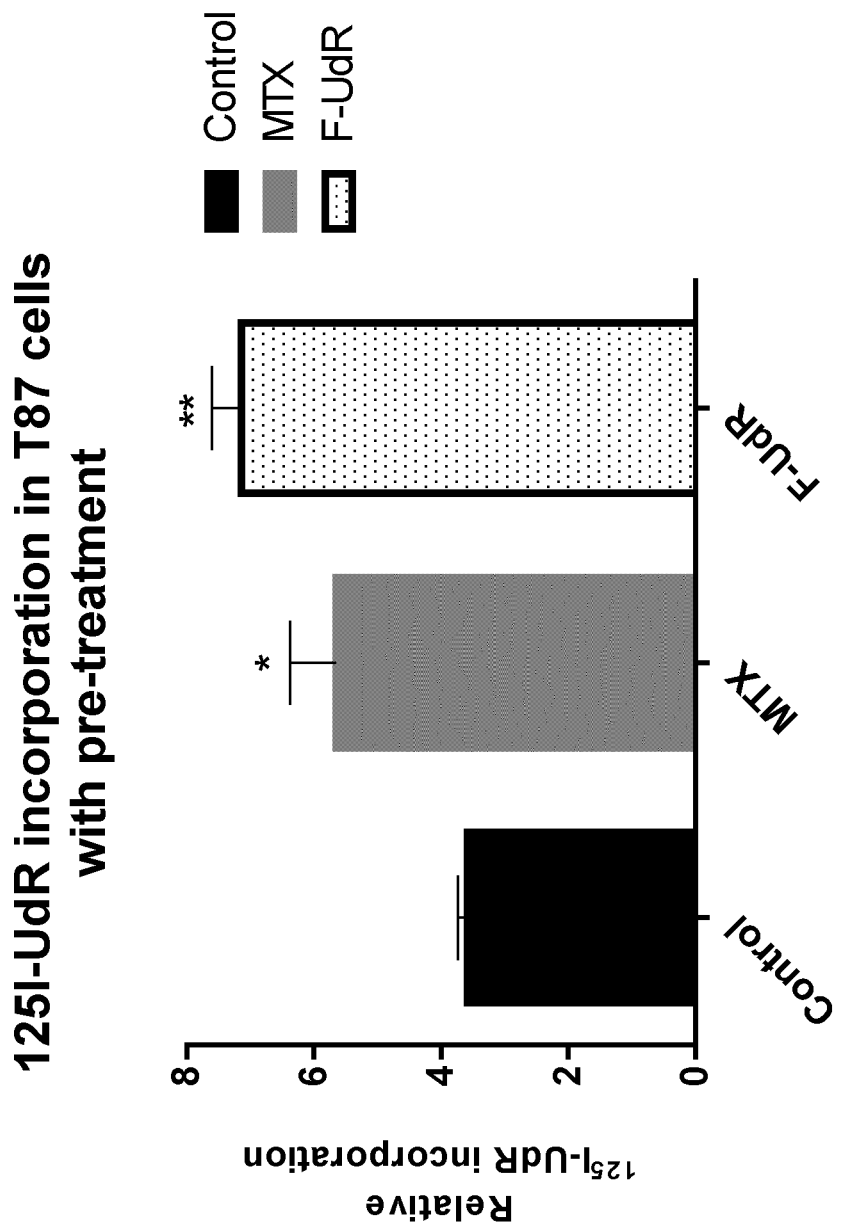

FIG. 13: $^{125}$I-UdR incorporation in T87 GBM cells in vitro after MTX/F-UdR exposure.

A) 1 hour pre-treatment of T87 GBM cells in vitro with 1 µM MTX or F-UdR before $^{125}$I-UdR exposure increased the $^{125}$I incorporation in the cells. The cells were washed twice after the pretreatment and incubated for 16 h before 100 Bq/mL $^{125}$I-UdR was added. After 72 h exposure the cells were washed again to get rid of excess $^{125}$I-UdR. The incorporation rate was determined by a gammacounter. Both MTX and F-UdR pretreatment could significantly increase the $^{125}$I-UdR incorporation in the cells compared to non-treated control cells.

B) The same was found for co-incubation of the T87 GBM cells with increasing concentrations of MTX or F-UdR and 18.5 KBq/mL 125I-UdR for 4 hours. F-UdR was effective in concentrations ≥1 nM while MTX was effective at ≥10 nM. At a F-UdR concentration of 10 µM, the 125I-incorporation declined presumably do to toxic effects from the F-UdR.

C) The same was found for co-incubation of the slowly dividing GBM cell line T86 with MTX/F-UdR and $^{125}$I-UdR for 4 hours. Opposed to the T87 cell line, the T86 cell line is also known to have an unmethylated MGMT promoter region, thereby being less responsive to TMZ chemotherapy.

Figure 14:
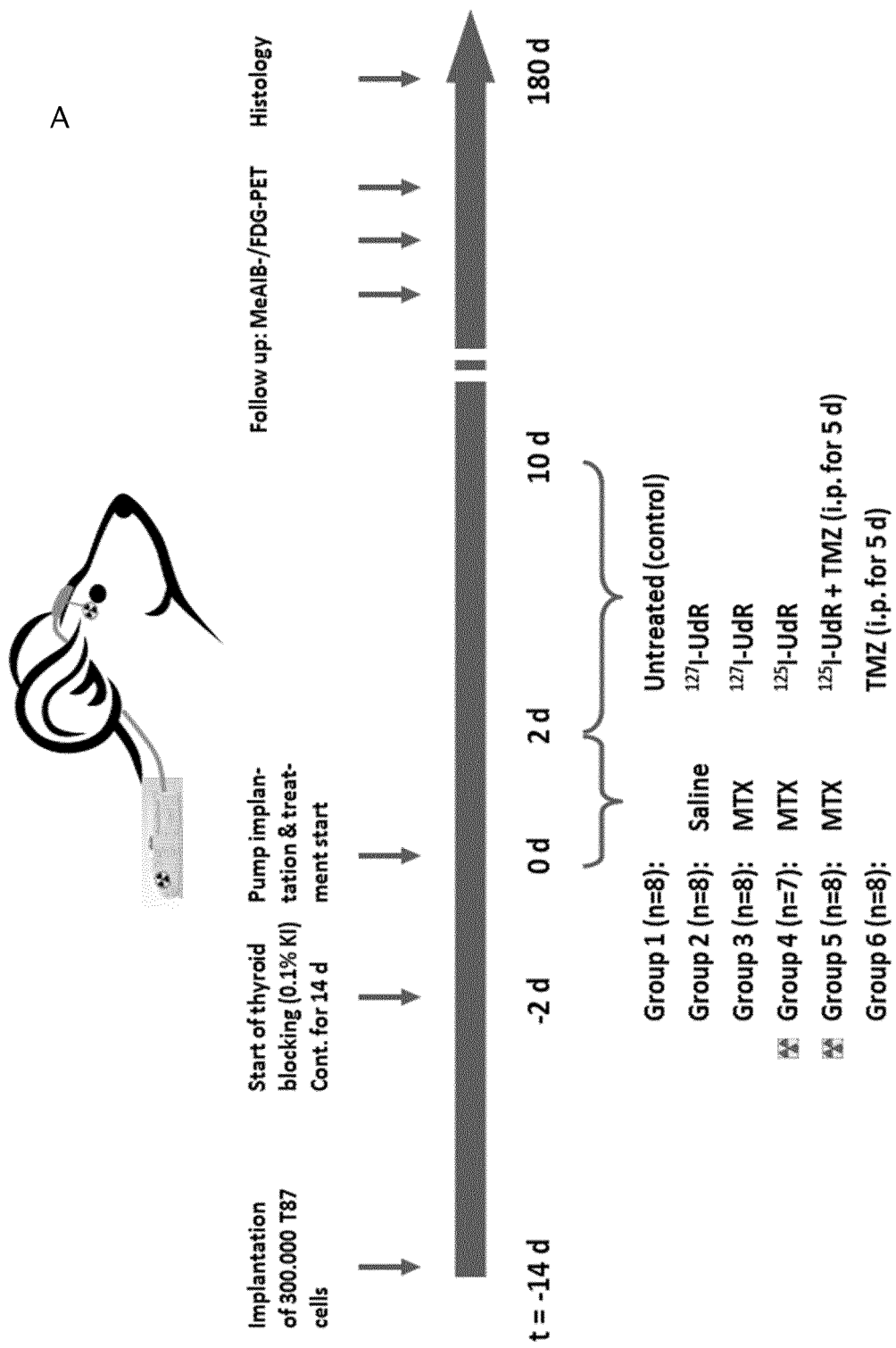

FIG. 14: A) In a continuation of the study illustrated in FIG. 4, groups 1, 3 and 6 were added to the in vivo therapeutic study using the orthotopic GBM rat model. B) A KM-survival plot comprising all studies groups. The median survival of the untreated group, the MTX+127I-UdR group and the TMZ-alone group was 24 d, 30.5 d and 47 d, respectively.

DETAILED DESCRIPTION OF THE INVENTION

Terms and Definitions

To facilitate the understanding of the following description, a number of definitions are presented in the following paragraphs.

The term "treatment", as used anywhere herein comprises any type of therapy, which aims at terminating, preventing, ameliorating and/or reducing the susceptibility to a clinical condition as described herein. Thus, "treatment," "treating," and the like, as used herein, refer to obtaining a desired pharmacologic and/or physiologic effect, covering any treatment of a pathological and/or clinical condition or disorder in a mammal, including a human. The effect may be prophylactic in terms of completely or partially preventing a disorder or symptom thereof and/or may be therapeutic in terms of a partial or complete cure for a disorder and/or adverse effect attributable to the disorder. That is, "treatment" includes (1) preventing the disorder or clinical condition from occurring or recurring in a subject, (2) inhibiting the disorder or clinical condition, such as arresting its development, (3) stopping or terminating the disorder or clinical condition or at least symptoms associated therewith, so that the host no longer suffers from the disorder or clinical condition or its symptoms, such as causing regression of the disorder or clinical condition or its symptoms, for example, by restoring or repairing a lost, missing or defective function, or stimulating an inefficient process, or (4) relieving, alleviating, or ameliorating the disorder or clinical condition, or symptoms associated therewith, where ameliorating is used in a broad sense to refer to at least a reduction in the magnitude of a parameter, such as inflammation, pain, and/or immune deficiency.

The terms "ameliorate", "ameliorating" and "amelioration", are also used separately herein to refer to a reduction of the severity of the occurrence of symptoms or characteristics of a disorder or clinical condition.

High-Grade Gliomas

The methods, uses, agents, compositions and kits-of-parts provided herein are generally intended for treating and/or ameliorating any intracerebral solid neoplasm. This includes all tumors inside the human skull (cranium) or in the central spinal canal. The tumor may originate from the brain itself, but also from lymphatic tissue, blood vessels, the cranial nerves, the brain envelopes (meninges), skull, pituitary gland, or pineal gland. Within the brain itself, the involved cells may be neurons or glial cells (which include astrocytes, oligodendrocytes, and ependymal cells). Brain tumors may also spread from cancers primarily located in other organs (metastatic tumors).

In one preferred embodiment, the solid neoplasm is a brain tumor involving glial cells, and a preferred embodiment, the methods, uses, agents, compositions and kits-of-parts provided herein are intended for treating and/or ameliorating a high-grade glioma. High-grade gliomas are undifferentiated or anaplastic tumor. Of numerous grading systems in use, the most common is the World Health Organization (WHO) grading system for astrocytoma, under which tumors are graded from I (least advanced disease—best prognosis) to IV (most advanced disease—worst prognosis). In this grading system, high-grade gliomas are categorized by the World Health Organization (WHO) as grade III and IV gliomas. These tumors are malignant and carry a worse prognosis.

High-grade gliomas include anaplastic astrocytomas (WHO grade III) and glioblastoma multiforme (WHO grade IV). Thus, in one embodiment, the methods, uses, agents, compositions and kits-of-parts provided herein are intended for treating and/or ameliorating anaplastic astrocytomas and/or glioblastoma multiforme. Glioblastoma multiforme presents two variants, giant cell glioblastoma and gliosarcoma, both of which are the subject of treatment according to the present invention. Glioblastoma multiforme tumors are characterized by the presence of small areas of necrotizing tissue that is surrounded by anaplastic cells. This characteristic, as well as the presence of hyperplastic blood vessels, differentiates the tumor from Grade 3 astrocytomas, which do not have these features.

Glioblastoma exists as a "classical" subtype, a "proneural" subtype and a "mesenchymal" subtype. Most tumors of the classical subtype have extra copies of the epidermal growth factor receptor (EGFR) gene, and have elevated expression of epidermal growth factor receptor (EGFR), while the TP53 gene, which is often mutated in glioblastoma, is rarely mutated in this subtype.

The proneural subtype often has high rates of alterations in the TP53 gene, and the PDGFRA gene, which encodes a-type platelet-derived growth factor receptor, and the IDHI gene, which encodes isocitrate dehydrogenase-1. The mesenchymal subtype is has mutations in the NF1 gene, which encodes neurofibromatosis type 1.

Many other genetic alterations have been identified in glioblastoma, and many are clustered in three pathways involving P53, RB, and PI3K/AKT. Another important alteration is methylation of the DNA repair enzyme MGMT.

Glioblastomas usually form in the cerebral white matter, grow quickly, and can become very large before producing symptoms. Some glioblastomas form more slowly following de-differentiation of low-grade astrocytoma or anaplastic astrocytoma. These are called secondary Glioblastomas. The tumor may extend into the meninges or ventricular wall, leading to high protein content in the cerebrospinal fluid (CSF) (>100 mg/dL), as well as an occasional pleocytosis of 10 to 100 cells, mostly lymphocytes. Rarely, malignant cells carried in the CSF may spread to the spinal cord or cause meningeal gliomatosis. However, metastasis of glioblastomas beyond the central nervous system is very unusual. About half of the glioblastomas occupy more than one lobe of a hemisphere or are bilateral. Tumors of this type usually arise from the cerebrum and may rarely exhibit the classic infiltration across the corpus callosum, producing a butterfly (bilateral) glioma.

The tumor may take on a variety of appearances, depending on the amount of haemorrhage, necrosis, or its age. Contrast-enhanced T1-weighted MRI (magnetic resonance imaging) will usually show an inhomogeneous mass with central necrosis and a variable ring of enhancement surrounded by edema. Mass effect from the tumor and edema may compress the ventricles and cause hydrocephalus.

Cancer cells with stem cell-like properties have been found in glioblastomas. The presence of cancer stem cells is a likely cause of the resistance of glioblastomas to conventional treatments, and their high recurrence rate.

Active Agents

The methods, uses, agents, compositions and kits-of-parts provided herein are intended for treating and/or ameliorating an intracerebral solid neoplasm and involve the use of a radioactive agent characterized by short-range cytotoxic ionizing radiation, wherein the radioactive agent is preferably administered directly to the tumor site by convection-enhanced delivery. In a preferred embodiment, the use of a radioactive agent is combined with a chemotherapeutic agent, which can be administered systemically to the subject in need of treatment. The treatment involving the radioactive agent may also be combined with a further therapeutic agent, such as an adjuvant or neoadjuvant. In one embodiment, the methods, uses, agents, compositions and kits-of-parts provided herein, involves the combined use of a radioactive agent characterized by short-range cytotoxic ionizing radiation and a further therapeutic agent, such as an adjuvant or neoadjuvant, wherein said radioactive agent and further therapeutic agent are administered by intracerebral convection-enhanced delivery, and preferably further involve an additional chemotherapeutic agent, which is preferably administered systemically to the subject in need of treatment.

Radioactive Agents

The radioactive agents provided herein are characterized by a short-range cytotoxic ionizing radiation. The radioactive agent preferably comprises an Auger electron emitting radioisotope. Thus, in this embodiment, the solid neoplasm is targeted by Auger electron therapy. Auger electron therapy is a radiation therapy for the treatment of cancer that relies on large numbers of low-energy electrons emitted from the radioisotopes that damage cancer cells via the "Auger effect", rather than the high-energy forms of radiation more traditionally used in radiation therapy. In parallel with conventional radiation therapy, Auger electron therapy relies on radiation-induced damage to cancer cells—particularly DNA damage—in order to arrest cell division, stop tumor growth and metastasis, and consequently kill existing tumor cells. It differs from other forms of radiation therapy because the electrons emitted in the radioactive decay, the Auger electrons, are released in large numbers with low kinetic energy, leading to high linear-energy-transfer (LET) effects. Because of their low energy these electrons exert their damaging effect on cellular structures over a very short nanometre scale range being less than the size of a single cell. This very short-range delivery of energy provides a highly targeted therapy, because the radiation-emitting nuclide is located inside the cell to cause damage to the genomic DNA.

In one embodiment, the radioactive agent of the invention comprises an Auger electron emitting radioisotope selected from $^{77}$Br, $^{80m}$Br, $^{123}$I, $^{124}$I, $^{125}$I or $^{126}$I. In another embodiment, the radioactive agent comprises a radioisotope selected from the group consisting of the α-emitter $^{211}$At or the β$^-$-emitter $^{131}$I. Thus, in one embodiment, the radioactive agent comprises a radioisotope selected from the group consisting of $^{77}$Br, $^{80m}$Br, $^{123}$I, $^{124}$I, $^{125}$I, $^{126}$I and $^{211}$At. In a preferred embodiment, the radioisotope is $^{125}$I.

The radioactive agent may also in one embodiment consist of or comprise an Auger-electron emitting radionucleoside or an analogue or a prodrug thereof. For example, the radioactive agent may comprise or consist of a halogenated nucleoside analogue, 5-[$^{123}$I]-iodouridine T-deoxyribonucleoside, 5-[$^{124}$I]-iodouridine 2'-deoxyribonucleoside, 5-[$^{125}$I]-iodouridine 2'-deoxyribonucleoside, 5-[$^{77}$Br]-bromouridine T-deoxyribonucleoside, 5-[$^{80m}$Br]-bromouridine 2'-deoxyribonucleoside, 8-[$^{123}$I]-iodoadenine 2'-deoxyribonucleoside, 8-[$^{124}$I]-iodoadenine T-deoxyribonucleoside, 8-[$^{125}$I]-iodoadenine 2'-deoxyribonucleoside, 5-[$^{211}$At]-astatouridine 2'-deoxyribonucleoside, or 8-[$^{211}$At]-astatoadenine T-deoxyribonucleoside.

The radioactive agent may also comprise or consist of a prodrug of a halogenated nucleoside analogue, 5-[$^{123}$I]-iodouridine T-deoxyribonucleoside, 5-[$^{124}$I]-iodouridine 2'-deoxyribonucleoside, 5-[$^{125}$I]-iodouridine 2'-deoxyribonucleoside, 5-[$^{77}$Br]-bromouridine T-deoxyribonucleoside, 5-[$^{80m}$Br]-bromouridine 2'-deoxyribonucleoside, 8-[$^{123}$I]-iodoadenine 2'-deoxyribonucleoside, 8-[$^{124}$I]-iodoadenine T-deoxyribonucleoside, 8-[$^{125}$I]-iodoadenine 2'-deoxyribonucleoside, 5-[$^{211}$At]-astatouridine 2'-deoxyribonucleoside, or 8-[$^{211}$At]-astatoadenine T-deoxyribonucleoside. In one embodiment, the prodrug comprises a 3' or a 5' carboxylate or phosphate ester of the halogenated nucleoside analogue.

In one particularly preferred embodiment, the radioactive agent consists of or comprises 5-[$^{125}$I]iodo-2'-deoxyuridine, also sometimes designated 5-[$^{125}$I]iododeoxyuridine, 5-[$^{125}$I]-iodouridine or $^{125}$I-UdR.

Further Therapeutic Agents

The methods, uses, agents, compositions and kits-of-parts provided herein for treating and/or ameliorating an intracerebral solid neoplasm by delivery of a radioactive agent, preferably by intracerebral convection-enhanced, is preferably combined with a further agent, which enhances the therapeutic effect of the radioactive agent. Thus, the use of a radioactive agent as provided herein, where the radioactive agent is administered by convention-enhanced delivery may also be combined with the use or administration of at least one further therapeutic agent. The further therapeutic agent is preferably administered by intracerebral convention-enhanced delivery. Most conveniently, the further therapeutic agent is co-administered with the radioactive agent by convection-enhanced delivery. The term, "co-administration" is meant to imply that the radioactive agent and further therapeutic agent are administered concomitantly. Thus, in this case, it is preferred that the radioactive agent and further therapeutic agent are combined in a liquid solution prepared for administration by convention-enhanced delivery.

The further therapeutic agent may for example be an adjuvant or neoadjuvant. The further therapeutic agent is for example a thymidylate synthetase inhibitor, such as methotrexate, or 5-fluoro-2'-deoxyuridine (F-UdR), or non-radioactive 5-iodo-2'-deoxyuridine (I-UdR). Thus, in one embodiment, the further therapeutic agent is selected from the group consisting of thymidylate synthetase inhibitor (such as methotrexate), 5-fluoro-2'-deoxyuridine (F-UdR), and non-radioactive 5-iodo-2'-deoxyuridine (I-UdR). In a preferred embodiment, the further therapeutic agent is methotrexate (MTX). However, in another preferred embodiment, the further therapeutic agent is F-Udr.

Chemotherapeutic Agents

The use of a radioactive agent as provided herein and optionally the combined use of a radioactive agent and a further therapeutic agent as described herein above, is in a preferred embodiment, combined with the use or administration of at least one additional agent, which is suitable for treating or ameliorating a high-grade glioma, such as glioblastoma multiforme. The agent is preferably a chemotherapeutic agent. Any chemotherapeutic agent suitable for treatment of an intracerebral solid neoplasm, in particular high-grade gliomas such as glioblastoma multiforme, may be applied. The chemotherapeutic agent is preferably administered by systemic administration, for example by intravenous injection of a solution comprising the chemotherapeutic agent or by oral administration. The chemotherapeutic agent may be selected from alkylating agents, anti-metabolites, anti-microtubule agents, topoisomerase inhibitors and cytotoxic antibiotics.

In one embodiment, the chemotherapeutic agent is an alkylating agent. An alkylating agent is used in cancer treatment as an antineoplastic agent that attaches an alkyl group ($C_nH_{2n+1}$) to DNA. The alkyl group is attached to the guanine base of DNA, at the number 7 nitrogen atom of the purine ring. Since cancer cells, in general, proliferate faster and with less error-correction than healthy cells, cancer cells are more sensitive to DNA damage, alkylated DNA. Dialkylating agents can react with two different 7-N-guanine residues, and monoalkylating agents can react only with one 7-N of guanine.

Examples of alkylating agents are Nitrogen mustards, such as Cyclophosphamide, Mechlorethamine or mustine (HN2) (trade name Mustargen), Uramustine or uracil mustard, Melphalan, Chlorambucil, Ifosfamide and Bendamustine.

Other examples are Nitrosoureas, such as Carmustine, Lomustine and Streptozocin. In another embodiment, the alkylating agent is an Alkyl sulfonate, such as Busulfan. In another embodiment, the agent is Thiotepa or an analogue thereof.

The chemotherapeutic agent may also be a Platinum-based chemotherapeutic agent, which acts as an alkylating agent. These agents do not have an alkyl group, but nevertheless damage DNA, by permanently coordinating to DNA to interfere with DNA repair. These agents are sometimes referred to as "alkylating-like". Such agents include Cisplatin, Carboplatin, Nedaplatin, Oxaliplatin, Satraplatin, and Triplatin tetranitrate.

In yet another embodiment, the chemotherapeutic agent is an alkylating agent selected from procarbazine, altretamine, tetrazines, such as dacarbazine, mitozolomide and temozolomide.

In one embodiment, the chemotherapeutic agent is an alkylating agent, a topoisomerase inhibitor, such as Irinotecan, which targets type 1 topoisomerase or Etoposide, which targets type 2 topoisomerase. In another embodiment, the chemotherapeutic agent is a vascular endothelial growth factor (VEGF) inhibitor, such as Bevazizumab.

In another embodiment, the chemotherapeutic agent is selected from Nitrogen mustards, such as Cyclophosphamide, Mechlorethamine or mustine (HN2) (trade name Mustargen), Uramustine or uracil mustard, Melphalan, Chlorambucil, Ifosfamide and Bendamustine. In another embodiment, the chemotherapeutic agent is selected from Nitrosoureas, such as Carmustine, Lomustine and Streptozocin. In another embodiment, the chemotherapeutic agent is selected from Alkyl sulfonates, such as Busulfan. In another embodiment, the chemotherapeutic agent is Thiotepa or an analogue thereof. In another embodiment, the chemotherapeutic agent is selected from Platinum-based chemotherapeutic agents, such as Cisplatin, Carboplatin, Nedaplatin, Oxaliplatin, Satraplatin, and Triplatin tetranitrate. In another embodiment, the chemotherapeutic agent is selected from procarbazine, altretamine or tetrazines, such as dacarbazine, mitozolomide and temozolomide. In another embodiment, the chemotherapeutic agent is selected from topoisomerase inhibitors such as amsacrine, etoposide, etoposide phosphate, teniposide, doxorubicin, irinotecan, topotecan, exatecan, lurtotecan. In yet another embodiment, the chemotherapeutic agent is selected from VEGF inhibitors, such as bevacizumab and ranibizumab.

In a preferred embodiment, the chemotherapeutic agent is temozolomide (TMZ). Temozolomide (brand names Temodar and Temodal and Temcad) is chemotherapy agent, which is usually administered orally or by intraveneous injection. Temozolomide is a prodrug and an imidazotetrazine derivative of the alkylating agent dacarbazine.

Combination Treatment

As mentioned herein above, the provided methods, uses, compounds, compositions and kits-of-parts encompass treating or ameliorating intracerebral solid neoplasms, in particular high-grade gliomas, such as glioblastoma, preferably by intracerebral convection-enhanced delivery of a radioactive agent characterized by a short-range cytotoxic ionizing radiation, are preferably combined with the administration or use of at least one further therapeutic agent and/or at least one additional chemotherapeutic agent.

The combinations of radioactive agent, further therapeutic agent and/or additional chemotherapeutic agent may be administered concurrently, sequentially, or intermittently, once or repeatedly, using various schedules of administration. When used sequentially, the further therapeutic agent is preferably administered prior to the radioactive agent.

The further therapeutic agent is preferably administered by intracerebral convection-enhanced delivery. This further agent can be provided by simultaneous, separate or sequential administration, but is preferred that the agent is provided by simultaneous administration.

The chemotherapeutic agent is preferably administered by systemic administration, for example as a capsule, in particular, if the chemotherapeutic agent is temozolomide. However, systemic administration by intravenous injection is also contemplated, and in general chemotherapeutic agents are preferably administered by intravenous injection.

In one embodiment, a radioactive agent characterized by a short-range cytotoxic ionizing radiation is provided for use in treating or ameliorating a high-grade glioma, wherein the agent is preferably administered by intracerebral convection-enhanced delivery, and wherein said use is combined with temozolomide for use treating or ameliorating the high-grade glioma, and temozolomide is preferably administered systemically.

Accordingly, a method is provided for treating or ameliorating a high-grade glioma comprising
    administering a radioactive agent characterized by a short-range cytotoxic ionizing radiation, and
    administering a chemotherapeutic agent, such as preferably temozolomide to a person in need thereof.

This method may also comprise administering one or more adjuvants or neoadjuvants, such as methotrexate or F-Udr. In particular, co-administration of the one or more adjuvants, such as methotrexate or F-Udr, with the radioactive agent by intracerebral convection-enhanced delivery is preferred, Thus, concomitant administration of the radioactive agent and F-Udr is particularly preferred.

In a particularly preferred embodiment, the radioactive agent is 5-[$^{125}$I]-iodo-2'-deoxyuridine ($^{125}$I-UdR) administered by convection-enhanced delivery and the chemotherapeutic agent is temozolomide administered systemically. In one further specific embodiment, methotrexate is a further agent co-administered with ($^{125}$I-UdR). In another embodiment, non-labeled I-Udr is a further agent co-administered with ($^{125}$I-UdR). In one particularly preferred embodiment, F-UdR is co-administered with ($^{125}$I-UdR).

Administration and Dosages

The radioactive agent employed in the methods, compounds, compositions and kit-of-parts provided herein is administered by intracerebral administration, which includes administration through the skull (cranium) and into the central spinal canal. Direct intracerebral administration bypasses the blood-brain barrier.

Furthermore, all dividing cells take up and incorporate nucleic acid analogues, such as $^{125}$I-UdR, during DNA synthesis, and therefore, systemic administration of such radioactive agents is not preferred.

In a preferred embodiment, the radioactive agent is administered by convection-enhanced delivery (CED). Convection-enhanced delivery involves the continuous infusion of a therapeutic compound under positive pressure. One or more catheters can be placed using intraoperative neuronavigation into areas of residual tumor, preferably after surgical removal of the tumor. The one or more catheters are then connected to a pump, either an internal or external pump depending on the duration of the infusion. This convection-enhanced delivery bypasses the blood-brain barrier and allows the creation of higher concentrations of the radioactive agent in the brain with no or very little systemic toxicity.

In the methods, uses, agents, compositions and kits-of-parts provided herein, where the administration of a radioactive agent is combined with the use or administration of at least one further therapeutic agent, such as an adjuvant or neoadjuvant, it is preferred that said further therapeutic agent is also administered by convection-enhanced delivery.

The infusion rate for the convection-enhanced delivery can be adjusted to a level, which ensures sufficiently high delivery of the one or more therapeutic agents, while at same time avoiding adverse effects resulting from increased pressure in the skull. The infusion rate is should generally be about 0.1-5 ml/hour, and preferably between 0.1-4 ml/hour, such as 0.1-3 ml/hour, such as 0.1-2 ml/hour, such as preferably 0.1-1 ml/hour. Alternatively, the infusion rate is between 0.2-4 ml/hour, such as 0.2-3 ml/hour, such as 0.2-2 ml/hour, such as 0.3-2 ml/hour, such as 0.3-1.5 ml/hour, such as preferably 0.3-1.0 ml/hour, such as 0.3-0.9 ml/hour, such as 0.3-0.7 ml/hour, such as about 0.5 ml/hour.

Thus, the radioactive agent and optionally said further therapeutic agent is preferably administered at an infusion rate of 0.1-5 ml/hour, and preferably between 0.1-4 ml/hour, such as 0.1-3 ml/hour, such as 0.1-2 ml/hour, such as preferably 0.1-1 ml/hour, or at an infusion rate between 0.2-4 ml/hour, such as 0.2-3 ml/hour, such as 0.2-2 ml/hour, such as 0.3-2 ml/hour, such as 0.3-1.5 ml/hour, such as preferably 0.3-1.0 ml/hour, such as 0.3-0.9 ml/hour, such as 0.3-0.7 ml/hour, such as about 0.5 ml/hour.

In one embodiment, the radioactive agent and optionally said further therapeutic agent is administered at an infusion rate of 0.1-5.0 ml/hour, preferably about 0.5 ml/hour.

The radioactive agent and, optionally, the further therapeutic agent is administered in one or more fractions, with an appropriate timely interval between each fraction. For example, the radioactive agent and optionally the further therapeutic agent is administered in 1-20 fractions, such as 1, 2, 3, 4, 5, 6, 7, 8, 9, 10, 11, 12, 13, 14, 15, 16, 17, 18, 19, or 20 fractions. In a preferred embodiment, the radioactive agent and optionally the further therapeutic agent is administered by convection-enhanced therapy in 1-10 fractions, such as 1-9 fractions, such as 1-8 fractions, such as 1-7 fractions, such as 1-6 fractions, such as 1-5 fractions. The radioactive agent and, optionally, the further therapeutic agent is preferably administered in 1-5 fractions, most preferred in 5 fractions.

The time between each fraction may vary depending on the patient response and practical considerations. The time between each fraction will usually vary between a few hours and several days. In a preferred embodiment, one fraction per day is provided, but the fractions may also be provided once a week.

Each fraction comprises or consists of one or more infusions of radioactive agent and, optionally, one or more infusions of the further therapeutic agent. In one preferred embodiment, one fraction comprises or consists of one or more initial infusions with the further therapeutic agent, such as adjuvant or neoadjuvant, for example F-Udr or methotrexate, and one or more subsequent infusions of radioactive agent, such as $^{125}$I-UdR.

The duration of the infusions may also vary, depending on the chosen concentration of the radioactive agent and, optionally, the further therapeutic agent in the administered composition.

Typically, each infusion of the radioactive agent, such as $^{125}$I-UdR, will vary from 30 minutes to 30 days, preferably between 1 and 20 days, and more preferred 2 and 10 days, such as about five days.

Typically, each infusion of the further therapeutic agent, such as F-Udr or methotrexate, can vary from 10 minutes to 30 days, preferably between 1 hour and 10 days, and more preferred 1-5 days, such as about two days.

Thus, treatment regime could consist of 1-20 fractions as indicated above, consisting of 1 hour –10 days infusion of the further therapeutic agent (adjuvant or neoadjuvant, such as F-Udr or methotrexate) followed by 1 hour –10 days infusion with radioactive agent, such as $^{125}$I-UdR, followed by 1-20 days interval, for example with infusion of isotonic saline solution between infusions of radioactive agent and further therapeutic agent.

For example, a treatment regime could consist of a number of fractions as indicated above, consisting of 2 days infusion of the further therapeutic agent (adjuvant or neoadjuvant, such as F-Udr or methotrexate) followed by 5 days infusion with radioactive agent, such as $^{125}$I-UdR, followed by 7 days interval, for example with infusion of isotonic saline solution between infusions of radioactive agent and further therapeutic agent.

Without infusion of further therapeutic agent, a treatment regime could consist of 1-20 fractions as indicated above, consisting of 1 hour –10 days infusion with radioactive agent, such as $^{125}$I-UdR, followed by 1-20 days interval, for example with infusion of isotonic saline solution between infusions of radioactive agent and further therapeutic agent.

The treatment regime preferably comprises or consists of 5 fractions. The radioactive agent is provided in a therapeutically effective concentration. Each provided fraction may thus comprise between 1 kBq to 50 GBq of radioactive agent and optionally 1-25 mg of said further therapeutic agent (such as MTX or F-Udr). Thus, the composition provided may comprise 1 kBq to 50 GBq radioactive agent. The radioactive agent content of each fraction can be between 1 kBq to 50 GBq, such as 100 kBq to 40 GBq, such as 1 MBq to 40 GBq, such as 500 MBq to 30 GBq, such as 0.1 GBq to 20 GBq, such as 0.1-10 GBq, such as 0.1-9 GBq, such as 0.1-8 GBq, such as 0.1-7 GBq, such as 0.1-6 GBq, such as 0.1-5 GBq, such as 0.1-4 GBq, such as 0.1-3.7 GBq, such as 0.1-3 GBq, such as 0.1-2 GBq. In a preferred embodiment, the radioactive agent content of each fraction is 0.1-3.7 GBq, more specifically 0.1-3.0, such as 0.1-2.0 GBq, such as 0.2-2.0 GBq, such as 0.3-2.0 GBq, such as 0.4-2.0 GBq, such as 0.5-2.0 GBq, such as 0.6-2.0 GBq, such as 0.7-2.0 GBq, such as 0.8-2.0 GBq, such as 0.9-2 GBq, such as 1-2 GBq. In one embodiment, each fraction comprise 0.1-3.7 GBq, such as 0.2-3.7 GBq, such as 0.3-3.7 GBq, such as 0.4-3.7 GBq, such as 0.5-3.7 GBq, such as 0.6-3.7 GBq, such as 0.7-3.7 GBq, such as 0.8-3.7 GBq, such as 0.9-3.7 GBq, such as 1.0-3.7 GBq, such as 1.1-3.7 GBq, such as 1.23.7 GBq, such as 1.3-3.7 GBq, such as 1.4-3.7 GBq, such as 1.5-3.7 GBq, such as 1.6-3.7 GBq, such as 1.7-3.7 GBq, such as 1.8-3.7 GBq, such as 1.9-3.7 GBq, such as 2.0-3.7 GBq, such as 2.1-3.7 GBq, such as 2.2-3.7 GBq, such as 2.3-3.7 GBq, such as 2.4-3.7 GBq, such as 2.5-3.7 GBq, such as 2.6-3.7 GBq, such as 2.7-3.7 GBq, such as 2.8-3.7 GBq, such as 2.9-3.7 GBq, such as 3.0-3.7 GBq, 3.1-3.7 GBq, such as 3.2-3.7 GBq, such as 3.3-3.7 GBq, such as 3.4-3.7 GBq, such as 3.5-3.7 GBq, such as 3.6-3.7 GBq.

The further therapeutic agent, such as an adjuvant or neoadjuvant, is also administered in a therapeutically effective concentration. The specific amount of further therapeutic agent depends on the specific choice of agent. In general, each provided fraction may comprise between 0.01-5 mg/mL of said further therapeutic agent, such as adjuvant or neoadjuvant, for example methotrexate. However, F-Udr appears to be substantially more effective than methotrexate, and therefore, when F-Udr is chosen as a further agent, the concentration has to be adjusted accordingly. Thus, the composition provided may comprise between 0.01 microg to 5 mg/mL, such as 0.01-5 mg/mL or 0.01-5 microg/mL of a further therapeutic agent. The amount of further therapeutic agent in each fraction can be between 0.01-5 mg/mL, such as 0.01-4 mg/mL, such as 0.01-3 mg/mL, such as 0.01-2 mg/mL, such as 0.02-2 mg/mL, such as 0.03-2 mg/mL, such as 0.04-2 mg/mL, such as 0.05-2 mg/mL, such as 0.06-2 mg/mL, such as 0.07-2 mg/mL, such as 0.08-2 mg/mL, such as 0.09-2 mg/mL, such as 0.1-2 mg/mL, such as 0.2-2 mg/mL, such as 0.3-2 mg/mL, such as 0.4-2 mg/mL, such as 0.5-2 mg/mL, such as 0.5-1.9 mg/mL, such as 0.5-1.8 mg/mL, such as 0.5-1.7 mg/mL, such as 0.5-1.6 mg/mL, such as 0.5-1.5 mg/mL, such as 0.5-1.4 mg/mL, such as 0.6-1.4 mg/mL, such as 0.6-1.4 mg/mL, such as about 1 mg/mL. Preferably, each fraction comprise about 1 mg/mL of a further therapeutic agent, such as about 1 mg/mL methotrexate. For F-Udr, the preferred range is 0.01-5 microg/mL, more preferred around 0.5-2.5 microg/mL.

As mentioned above, the radioactive agent and optionally the further therapeutic agent is administered by convection-enhanced delivery. However, the methods, compounds, compositions and kit-of-parts provided herein also in a preferred embodiment involve the administration of at least one additional agent, such as a chemotherapeutic agent. The additional agent can be administered by any route available to the skilled person, including any administration methods, involving parenteral injections and oral and topical administration. Other drug-administration methods, such as subcutaneous injection, which are effective to deliver the drug to a target site or to introduce the drug into the bloodstream, are also contemplated. Furthermore, intranasal administration and administration by pulmonary inhalation is convenient and effective methods of administration, which could be used. The additional agent, such as chemotherapeutic agent, is preferably administered by a systemic administration method. Thus, in a preferred embodiment, the additional agent is administered enterally or parenterally. Thus, in one embodiment, the additional chemotherapeutic agent administered enterally, that is by oral administration or parenterally, that is by intravenous, intramuscular, subcutaneous, intranasal, intrarectal, intravaginal or intraperitoneal administration. The subcutaneous and intramuscular forms of parenteral administration can be used; however, intravenous injections are generally preferred. Appropriate dosage forms for such administration may be prepared by conventional techniques.

The additional chemotherapeutic agent is preferably administered in an amount between 1-350 mg/m$^2$ or 5-15 mg/kg. For example, the additional chemotherapeutic agent can be administered in an amount 0.1 mg/m$^2$ to 500 mg/m$^2$ or 1 mg/kg to about 100 mg/kg per day. The exact dosage depends on the specific chemotherapeutic agent. For example, if the agent is bevazizumab, it is administered preferably in an amount between 5-15 mg/kg, such as about 10 mg/kg body weight.

In a preferred embodiment, the additional chemotherapeutic agent is temozolomide and is administered systemically; such as by oral capsules, in an amount of 75-200 mg/m$^2$, such as 100-200 mg/m$^2$, such as about 150 mg/m$^2$.

The additional chemotherapeutic agent is preferably administered in combination with a radioactive agent as described herein, and optionally at least one further therapeutic agent, such as an adjuvant and/or neoadjuvant. These different therapeutic agents may be administered simultaneously, either as separate formulations or combined in a unit dosage form, or administered sequentially. However, the adjuvant and/or neoadjuvant is preferably co-administered with the radioactive agent by convection-enhanced delivery In general, the dosage requirements will vary with the particular composition employed, the route of administration and the particular individual being treated. Ideally, an individual to be treated by the present method will receive a pharmaceutically effective amount of the agent, composition or kit-of-parts in the maximum tolerated dose, generally no higher than that required before drug resistance develops.

The methods and uses of the present invention provide that a radioactive agent and optionally a further therapeutic agent, such as an adjuvant or neoadjuvant, and an additional chemotherapeutic agent is administered in an effective amount. By "effective amount" herein is meant a dose that produces the therapeutic effects for which it is administered. The exact dose will depend on the glioma to be treated, and can be ascertained by one skilled in the art using known techniques. Further, as is known in the art, adjustments for age as well as the body weight, general health, sex, diet, time of administration, drug interaction, the route and form of administration, and the severity of the clinical condition may be necessary, and will be ascertainable with routine experimentation by those skilled in the art.

Formulation

The radioactive agent provided for use in treating and/or ameliorating a high-grade glioma is preferably administered by convection-enhanced delivery. Also, the methods and uses provided herein may involve the combined use of the radioactive agent and a further therapeutic agent, which is also administered by convection-enhanced delivery. Thus, the radioactive agent and the further therapeutic agent are preferably formulated as a liquid composition, suitable for intracerebral convection-enhanced delivery. Thus, the formulation is preferably prepared for administration by convection-enhanced delivery.

For example, the radioactive agent and the additional therapeutic agent can be formulated in a liquid solution of isotonic saline buffer or PBS buffer, for example comprising ethanol. The presence of ethanol can serve to stabilize $^{125}$I-UdR and inhibit radiolysis. In fact, a composition suitable for administration by intracerebral convection-enhanced delivery may be provided initially as a concentrate comprising up 50% ethanol in order to increase shelf life of the composition. Prior to administration by convection-enhanced delivery, the solution can be diluted to obtain a suitable non-toxic ethanol concentration.

In one aspect, a composition is provided, which comprise a radioactive agent characterized by a short-range cytotoxic ionizing radiation, wherein said composition is prepared for administration by intracerebral convection-enhanced delivery. In one embodiment, the composition is a liquid solution of isotonic saline buffer or PBS buffer, optionally comprising ethanol. The composition my also comprise at least one further agent, for example an adjuvant, such as a thymidylate synthetase inhibitor, such as methotrexate, a nucleoside analogue, such as 5-fluoro-2'-deoxyuridine (F-UdR), or non-radioactive 5-iodo-2'-deoxyuridine (1-UdR). In one embodiment, the composition comprises 1 kBq to 50 GBq, preferably 0.1-3.7 Gbq, such as 0.1-2 GBq, radioactive agent and/or 0.01-5 microg/mL or 0.01-5 mg/mL of said further agent, the amount of agent depending on the choice of agent. For methotrexate, the preferred amount is 0.01-5 mg/mL, preferably 2.5 mg/mL, whereas F-Udr can be up to 1000 times more efficient, the administered amount of F-Udr is adjusted accordingly, and is preferably administered in an amount of 0.01-5 microg/mL.

The additional agent, such as methotrexate, can be provided as approximately 2.5 mg/ml in a composition for injection by convection-enhanced delivery. Thus, each ml of solution may contain 2.5 mg methotrexate (sodium salt formed in situ). When F-Udr is provided, the corresponding concentration can be around 0.5-2.5 microg/mL.

The treatment involving the radioactive agent defined herein above may also in a preferred embodiment be combined with one or more additional chemotherapeutic agents, preferably agents suitable for treatment of high-grade gliomas, such as glioblastoma. As mentioned above, one or more such additional chemotherapeutic agent is preferably administered systemically, for example by enteral or parenteral administration. Thus, an additional chemotherapeutic agent, such as temozolomide, is preferably formulated as a pharmaceutical composition suitable for the relevant systemic administration regime.

Liquid dosage forms for administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

To prepare the pharmaceutical compositions comprising the additional chemotherapeutic agent, an appropriate amount of the chemotherapeutic agent, or a prodrug thereof, in salt form or base form, is combined in an intimate admixture with a pharmaceutically acceptable carrier, which can take a wide variety of forms depending on the form of preparation desired for administration. These pharmaceutical compositions are desirably in unitary dosage form suitable for administration orally, rectally, percutaneously, parenterally or by pulmonary inhalation or intranasal administration. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

It is especially advantageous to formulate the aforementioned pharmaceutical compositions in dosage unit form for ease of administration and uniformity of dosage. As used in the specification and claims, unit dosage form refers to physically discrete units suitable as unitary dosages, each unit containing a predetermined quantity of active ingredient (s) calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

An additional chemotherapeutic agent, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. For example, in one embodiment, formulations containing about one (1) milligram of chemotherapeutic agent or, more broadly, about 0.01 to about ten (10) grams, per tablet, are suitable unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the chemotherapeutic agent generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the chemotherapeutic agent with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well-known suspending agents.

Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The additional chemotherapeutic agent of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or non-aqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

However, the additional chemotherapeutic agent may also be formulated for oral administration. In particular, if the agent is temozolomid, it is preferably administered orally, and the agent is preferably formulated as an oral composition, for example as an oral tablet or capsule or a liquid extract.

The pharmaceutical preparations are preferably in unit dosage forms. In such form, the preparation is subdivided into unit doses containing appropriate quantities of the additional chemotherapeutic agent. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: The Science and Practice of Pharmacy 1995, edited by E. W. Martin, Mack Publishing Company, 19th edition, Easton, Pa.

Target Group

The methods and uses provided herein involves administering an effective amount of a radioactive agent and optionally a further therapeutic agent and/or an additional chemotherapeutic agent to a person in need thereof.

Generally, "a person in need thereof" is a person, who suffers from, has suffered from or is at risk of suffering from a glioma, in particular a high-grade glioma, such as anaplastic astrocytomas and/or glioblastoma multiforme. Thus, a person in need thereof can be determined based on a clinical analysis of the symptoms known to associate with gliomas. The specific symptoms of gliomas depend on which part of the central nervous system is affected. A brain glioma can cause headaches, nausea and vomiting, seizures, and cranial nerve disorders as a result of increased intracranial pressure. A glioma of the optic nerve can cause visual loss. Spinal cord gliomas can cause pain, weakness, or numbness in the extremities. Gliomas do not metastasize by the bloodstream, but they can spread via the cerebrospinal fluid and cause drop metastases to the spinal cord.

The presence of a glioma, including high-grade gliomas, is usually determined by advanced cerebral images technologies. Usually, a person suspected of having a glioma is subject to magnetic resonance imaging (MRI) and/or computer tomography (CT) imaging, which can reveal the presence of different anomalies in the brain. When viewed with contrast-enhanced CT or MRI, gliomas, such as glioblastomas, often appear as ring-enhancing lesions. The appearance is not specific, however, as other lesions such as abscess, metastasis, tumefactive multiple sclerosis, and other entities may have a similar appearance. Imaging of tumor blood flow using perfusion MRI and measuring tumor metabolite concentration with MR spectroscopy can also be used for example in combination with standard MRI in the diagnosis of glioblastoma.

Definitive diagnosis of a suspected glioma upon CT or MR imaging usually involves a stereotactic biopsy or a craniotomy with tumor resection and pathologic confirmation. The tumor grade is based upon the most malignant portion of the tumor, and, therefore biopsy or subtotal tumor resection can result in undergrading of the lesion.

In a preferred embodiment, the person in need thereof, is a person for which a high-grade glioma has been determined by pathological analysis of a tumor sample. Thus, the method and uses provided herein for treatment of high-grade gliomas are preferably applied to a person, which has been subject to tumor resection, and for which a sample of the surgically removed tumor has been identified as a high-grade glioma by pathological analysis. Thus, in the methods and uses provided herein are preferably applied to a person in need thereof subsequent to tumor resection.

Kit-of-Parts

The present invention in one aspect provides a use of a radioactive agent characterized by a short-range cytotoxic ionizing radiation combined with at least one further therapeutic agent (such as an adjuvant and/or neoadjuvant) and/or an additional chemotherapeutic agent suitable for treating and/or ameliorating a high-grade glioma.

In one aspect of the present invention, the radioactive agent and the further therapeutic agent and/or the additional chemotherapeutic agent is provided as a kit-of-parts. Thus, a kit-of-parts is contemplated, which comprises a combined preparation comprising or containing a radioactive agent characterized by a short-range cytotoxic ionizing radiation and
- a) at least one additional therapeutic agent and/or
- b) at least one further agent, for the simultaneous, separate or sequential administration for treating or ameliorating a high-grade glioma.

Thus, a kit-of-parts is contemplated, which comprises 1) a radioactive agent characterized by a short-range cytotoxic ionizing radiation and 2) a further therapeutic agent, such as an adjuvant or neoadjuvant, for example F-Udr or methotrexate and/or an additional chemotherapeutic agent, as defined elsewhere herein. In particular, the additional chemotherapeutic agent is preferably suitable for treating or ameliorating a high-grade glioma, such as anaplastic astrocytomas and/or glioblastoma multiforme.

It is understood that a kit-of-parts is provided comprising a combined preparation comprising or containing 1) a radioactive agent characterized by a short-range cytotoxic ionizing radiation and 2) at least one further therapeutic agent and/or at least one additional chemotherapeutic agent, for the simultaneous, separate or sequential administration for treating or ameliorating a high-grade glioma.

Examples of further therapeutic agents are provided elsewhere herein and include adjuvant or neoadjuvant, for example F-Udr or methotrexate. Also examples of additional chemotherapeutic agents are provided elsewhere herein and include temozolomide. In a preferred embodiment, the at least one additional therapeutic agent is a chemotherapeutic agent suitable for treating or ameliorating a high-grade glioma, such as glioblastoma multiforme, Specifically, in the provided kit-of-parts, the at least one further agent is an adjuvant or a neoadjuvant, for example a thymidylate synthetase inhibitor, such as methotrexate, or a nucleoside analogue, such as 5-fluoro-2'-deoxyuridine (F-UdR), or non-radioactive 5-iodo-2'-deoxyuridine (1-UdR). In a preferred embodiment, the further agent is F-Udr. In another embodiment, the agent is MTX.

The kit-of-parts may also comprise a composition comprising a radioactive agent characterized by a short-range cytotoxic ionizing radiation, wherein said composition is prepared for administration by intracerebral convection-enhanced delivery. The composition is preferably a liquid solution of isotonic saline buffer or PBS buffer, optionally comprising ethanol. Moreover, the composition may comprise at least one further agent, for example an adjuvant, such as a thymidylate synthetase inhibitor, such as methotrexate, a nucleoside analogue, such as 5-fluoro-2'-deoxyuridine (F-UdR), or non-radioactive 5-iodo-2'-deoxyuridine (1-UdR). Moreover, the composition preferably comprises in the range of 1 kBq to 50 GBq, preferably 0.1-3.7 Gbq, for example 0.1-2 GBq, radioactive agent and optionally, 0.01-5 microg/mL, preferably 2.5 microg/mL or 0.01-5 mg/mL, preferably 2.5 mg/mL of said further agent; the exact concentration being dependent on the choice of agent. For methotrexate, the preferred concentration is 0.01-5 mg/mL, preferably 2.5 mg/mL, whereas for F-Udr the preferred concentration is 0.01-5 microg/mL, such as 2.5 microg/mL.

Thus, the kit-of-parts provided herein preferably comprise a radioactive agent and optionally a further agent (such as an adjuvant or neoadjuvant), which are provided in a solution prepared for convection-enhanced delivery.

In a preferred embodiment, the radioactive agent is 5-[$^{125}$I]-iodo-2'-deoxyuridine ($^{125}$I-UdR). Also in a preferred embodiment, additional agent is the chemotherapeutic agent, temozolomide. In yet another embodiment, the further agent is F-Udr. However, the further agent could also be methotrexate and/or I-Udr.

The term "kit-of-parts" as used herein designates a combined preparation containing, as active substance, a radioactive agent characterized by a short-range cytotoxic ionizing radiation and at least one additional chemotherapeutic agent suitable for treating or ameliorating a high-grade glioma or exacerbating the effect of a treatment of a high-grade glioma, such as glioblastoma multiforme, for the simultaneous, separate or sequential administration, for treating or ameliorating a brain tumor, such as glioblastoma multiforme. Preferably the radioactive agent and if relevant the at least one further therapeutic agent is formulated for convection-enhanced delivery and the additional chemotherapeutic agent if relevant is formulated for systemic administration to a person in need thereof. Examples of relevant agents and formulations are provided herein above.

The at least two individual components, such as for example three individual components of the kit-of-parts form a functional unit, i.e. a functional true combination through a purpose-directed application. Due to their use in the kit-of-parts of the invention, the two or three active ingredients (radioactive agent and additional therapeutic agent or chemotherapeutic agent) show a joint effect.

Treatment

It is within the scope of the present invention to provide methods, uses, agents, compositions and kits-of-parts for treating and/or ameliorating a high-grade glioma, such as anaplastic astrocytomas (WHO grade III) and glioblastoma multiforme (WHO grade IV). The methods and uses of the invention involve administering at least one radioactive agent characterized by a short-range cytotoxic ionizing radiation. This radioactive agent is preferably administered by intracerebral convection-enhanced delivery.

Thus, a method of treating or ameliorating a high-grade glioma is provided, which comprise administering a radioactive agent characterized by a short-range cytotoxic ionizing radiation to a person in need thereof. The radioactive agent is preferably administered by convection-enhanced delivery. More specifically, a method is provided of treating or ameliorating a high-grade glioma in a patient comprising intracerebral administration of a radioactive agent characterized by a short-range cytotoxic ionizing radiation by convection-enhanced delivery to a person in need thereof. However, the method may also comprise administering at least one additional therapeutic agent, such as a chemotherapeutic agent suitable for treating or ameliorating a high-grade glioma, this is in a preferred embodiment, temozolomide (TMZ). The additional agent, such as TMZ is preferably administered by systemic administration, for example by oral or parenteral (e.g. IV) administration.

The method may also comprise administering at least one further agent for simultaneous, separate or sequential administration with the radioactive agent. The further agent can be an adjuvant or neoadjuvant, e.g. a thymidylate synthetase inhibitor, such as methotrexate, or a nucleoside analogue, such as 5-fluoro-2'-deoxyuridine (F-UdR), or non-radioactive 5-iodo-2'-deoxyuridine (1-UdR). The further agent is preferably F-Udr. The at least one further adjuvant or neoadjuvant is preferably administered by intracerebral convection-enhanced delivery. In fact, the further agent, such as an adjuvant, and the radioactive agent are preferably co-administered by convection-enhanced delivery. Thus, a solution may be prepared, which comprise a mixture of the radioactive agent (e.g. $^{125}$I-UdR) and an adjuvant, such as F-Udr or methotrexate, where the solution is prepared in a buffer suitable for convection-enhanced delivery. This solution can be used to co-administer the radioactive agent and an adjuvant.

The radioactive agent preferably comprises an Auger electron emitting radioisotope, most preferred, the radioactive agent is 5-[125I]-iodo-2'-deoxyuridine (125I-UdR). The method is preferably used for treatment and/or amelioration of a high-grade glioma selected from anaplastic astrocytomas (WHO grade III) and glioblastoma multiforme (WHO grade IV).

The radioactive agent and optionally the further agent are preferably administered at an infusion rate of 0.1-5 ml/hour, preferably about 0.5 ml/hour, and the radioactive agent and optionally the further agent may be administered in 1-20 fractions, preferably 1-5 fractions. The method encompasses that each fraction comprises 1 kBq to 50 GBq of said radioactive agent and optionally 1-25 mg of said further agent (such as MTX or F-Udr).

In total, a composition comprising 1 kBq to 50 GBq, preferably 0.1-3.7 GBq, such as 0.1-2 GBq, radioactive agent is preferably administered. Similarly, a composition comprising 0.01 microg/mL to 5 mg/mL of said further agent is preferably administered, the exact concentration depending on the choice of agent.

Moreover, a radioactive agent characterized by a short-range cytotoxic ionizing radiation is provided for use in treating and/or ameliorating a high-grade glioma (WHO grade III-IV), wherein the radioactive agent is administered by intracerebral convection-enhanced delivery. Compositions and kits and kits-of-parts comprising a radioactive agent characterized by a short-range cytotoxic ionizing radiation are also provided for such use.

It is also an object of the present invention to provide a use of a radioactive agent characterized by a short-range cytotoxic ionizing radiation for the manufacture of a medicament for the treating or ameliorating a high-grade glioma. Such use may also be applied for compositions comprising the radioactive agent characterized by a short-range cytotoxic ionizing.

A pharmaceutical composition is also provided in the treatment of a high-grade glioma comprising a radioactive agent characterized by a short-range cytotoxic ionizing radiation. In particular, a pharmaceutical composition is provided in the treatment of a high-grade glioma in a human subject by intracerebral convection-enhanced delivery, said pharmaceutical composition comprising a radioactive agent characterized by a short-range cytotoxic ionizing radiation. In this regard, the invention also provides a medicament for use in the treatment or amelioration of a high-grade glioma in a human subject comprising a radioactive agent characterized by a short-range cytotoxic ionizing radiation, wherein the radioactive agent is to be administered by intracerebral convection-enhanced delivery.

Further provided is a use of a radioactive agent characterized by a short-range cytotoxic ionizing radiation for the treatment and/or amelioration of a high-grade glioma. For example, a use is provided of a radioactive agent characterized by a short-range cytotoxic ionizing radiation for the treatment of a high-grade glioma, wherein the radioactive agent is administered by intracerebral convection-enhanced delivery The invention also in one aspect relates to a use of a radioactive agent characterized by a short-range cytotoxic ionizing radiation characterized in that it is for the manufacture of a medicament for the treatment and/or amelioration of a high-grade glioma.

The use, treatment and/or amelioration of a high-grade glioma provided herein may also involve a further therapeutic agent and/or an additional chemotherapeutic agent, as defined elsewhere herein.

As indicated, the provided methods, uses, agents, compositions and kits-of-parts relates to both treating and/or a high-grade glioma. Thus, the methods, uses, agent, compositions and kits-of-parts may be applied in a person, which has been diagnosed with a high-grade glioma. In a preferred embodiment, the methods and uses are applied to a person in need thereof, subsequent to surgical tumor resection. Thus, the methods and uses can be applied in a person, in which a high-grade glioma has been surgically removed in order to prevent recurrence and/or treat any remaining neoplasms, including residual tumor tissue.

EXAMPLE

Introduction

Figure 1:
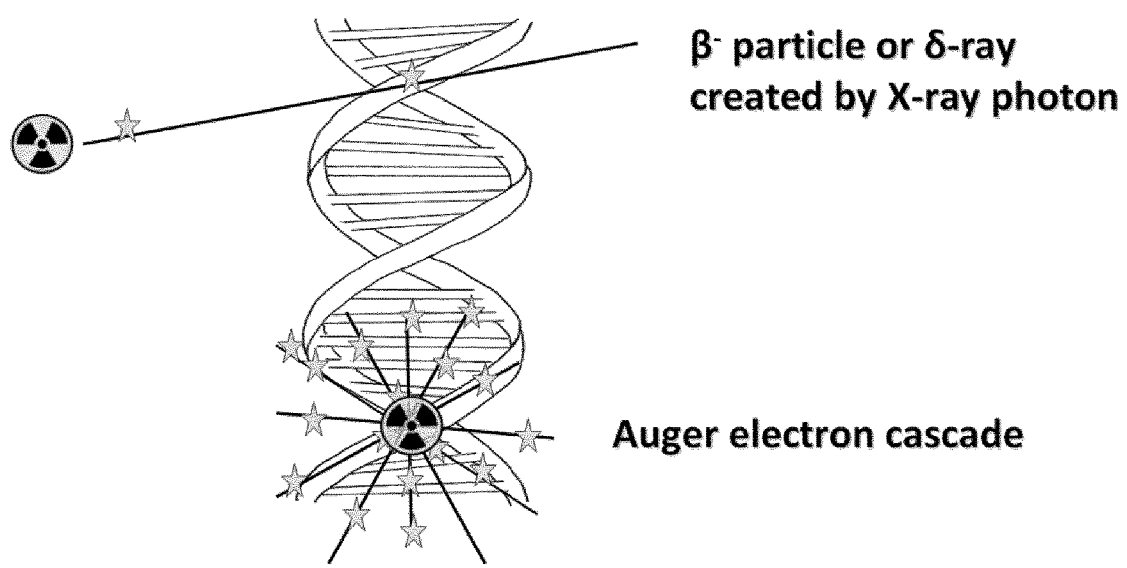
FIG. 1: Schematic view of the ionization pattern (stars) stemming from either the decay of an Auger-electron-emitting isotope with resulting cascade of Auger-electrons generating a densely ionized (high LET) region or the transversal of a sparsely ionizing β$^-$ particle or a δ-ray created by X-rays (both of low LET).

Glioblastomas (GBMs), the most common and malignant primary brain tumors, always recur after standard treatment. A novel promising therapeutic approach is short-range Auger-electron-emitters (AEEs). They exert a highly localized ionization density (high linear energy transfer (high-LET) (1, 2) (1, 2) (1, 2) (1, 2) (1, 2) (1, 2) (1, 2). This is a consequence of the emission of an electron cascade in each radioactive decay (FIG. 1), with all electrons having low energies and thus resulting in short-range destructive effects in biological tissue, limited to less than the diameter of a single cell. Therefore, AEEs are able to provide an extremely high local radiation dose, which may minimize toxic adverse effects to normal tissues due to cross-fire irradiation. However, this requires selective delivery of the AEEs to the genomic DNA of the cancer cells. The therapeutic effectiveness of DNA-incorporated AEEs, occurs mainly through extensive DNA damage from direct ionization of the DNA molecule (the direct effect) leading to clusters of DNA double strand breaks (DSBs) that are difficult for the cell to repair (high-LET effects). By contrast, in modern external radiotherapy high energy X-rays generate DSBs by low-LET 6-electrons (FIG. 1) via free radical formation (the indirect effect). Further, cancer stem cells are resistant to conventional external radiotherapy, which have been explained by the cancer stem cells' increased ability to repair DNA damage and to scavenge the free radicals formed in the external irradiation-induced cell eradication. This example aims to demonstrate that using the AEE compound [$^{125}$I]5-Iodo-2'-deoxyuridine ($^{125}$I-UdR, a thymidine analogue), which exerts its radiobiological effects predominantly via the direct effect, i.e. without free radicals, leading to complex DSBs from the high-LET Auger electron cascades, allows to effectively erdicate GBMs including the cancer stem cells both in vitro and in vivo.

Since all dividing cells take up and incorporate $^{125}$I-UdR during DNA synthesis and the biological half-life is very short (5 minutes), systemic administration in vivo to GBMs is not preferred. Accordingly, an alternative approach is required to use AEE-compounds for cancer stem cells-eradication in the brain. Convection-enhanced delivery (CED) involves the continuous infusion of a therapeutic compound under positive pressure. In practice, one or more catheters are placed using intraoperative neuronavigation into areas of residual tumor post tumor resection. The catheters are then connected to either an internal or external pump depending on the duration of the infusion. This bypasses the BBB and high concentrations of the therapeutic compound are created in the brain with no or very little systemic toxicity. As CED has the aforementioned properties, CED was used for delivery of $^{125}$I-UdR to GBMs in the present example.

Thus, in this example, the short-range Auger-electron-emitter (AEE) [$^{125}$I]5-Iodo-2'-deoxyuridine ($^{125}$I-UdR) was tested in an animal model. $^{125}$I-UdR is a radioactive AEE thymidine analogue that is incorporated into the DNA of dividing cells and upon decay causes clusters of double strand breaks leading to cell death. In vivo, $^{125}$I-UdR was administered by convection-enhanced delivery (CED) to by-pass the blood-brain barrier.

The overall aim of this example was to test the effect and safety profile of $^{125}$I-UdR therapy in vitro and in vivo. Moreover, it was determined if a synergistic effect could be achieved when combining $^{125}$I-UdR therapy with the currently used first-line chemotherapeutic agent temozolomide (TMZ).

Methods

Chemicals and Radiosyntheses $^{125}$I-UdR was prepared as follows: Sodium [$^{125}$I]iodide solution (1 vol. eq., approximately 13 MBq/μL) was transferred into a iodogen coated Eppendorf tube (coated with approximately 50 μg 1,3,4,6-tetrachloro-3a,6a-diphenylglycoluril) containing Dulbecco's phosphate buffered saline buffer (DPBS, 2.5 vol. eq.) and 5-Me$_3$Sn-2'-deoxyuridine (0.5 vol. eq., 1 μg/μl in dimethyl sulfoxide (DMSO)). The tube was gently agitated for 10 min at room temperature at which the reaction mixture was loaded on a Sep-Pak C18 plus short cartridge (activated prior to loading with EtOH (5 mL) and DPBS (5 mL)). The reaction tube was washed with DPBS (2 vol. eq.), which was transferred to the Sep-Pak cartridge. The cartridge was subsequently washed with DPBS (1 mL) and eluted with 50% EtOH in DPBS (2 mL) discarding the eluate without activity. The remaining active eluate was analyzed on HPLC (Gemini C18 150×4.6 cm, 5 micron, 20% MeOH (A) in 0.1% trifluoroacetic acid solution (B) (0-7 min); 20%→0% A, 80%→100% B (7-9 min); 100% B (9-16 min), 1 mL/min) to be 100% radiochemical pure. The final product was sterilized by passing the eluate through a 0.22 μm sterile filter into a capped vial. The amino-acid tracer [$^{11}$C]MeAIB was prepared as described previously.

Cell Culture

Cells were cultured as free-floating spheroids in the absence of serum at 36° C. in a humidified incubator with 5% CO$_2$. Two GSCs passage 9-12, designated T78 and T87, were utilized. They were established, as previously described in our laboratory in 2009 (T78) and 2010 (T87), in accordance with the Regional Scientific Ethical Committee (approval number S-VF-20040102). They have; the ability to form new spheroids at clonal density, a karyotype typical of GBMs, the ability to differentiate into cells expressing neuronal, astrocytic and oligodendrocyte markers upon culturering in serum-containing medium and the ability to form highly invasive tumors upon orthotopic xenografting (exemplified for the T87 GCS in Supplementary FIG. 1). Both GSCs have a hypermethylated 06-methylguanine-DNA methyltransferase (MGMT) promoter region and are derived from isocitrate dehydrogenase 1 (IDH1) negative tumors.

Viability Assay

T78 and T87 cells cultured as spheroids were trypsinized and seeded in 96-well plates (1000 and 2500 cells/well, respectively). The cells were then incubated in serum-free medium or serum-free medium containing either the non-radioactive, but chemically identical $^{127}$I-UdR (0.3 μg/ml, Sigma-Aldrich), or increasing activities of $^{125}$I-UdR (0-3 kBq/ml). At day 7, 20 μl of CellTiter Blue (Promega) was added and the cells were returned to the incubator for 6 hours prior to recording of the fluorescence in a Victor3 Multilabel Plate Reader (PerkinElmer Life Sciences).

Migration Assay

Geltrex (Gibco) and serum-free medium was mixed (1+49) and 1.4 ml was added to each well in 12-well plates. Coated plates were incubated over night at 36° C. and the following morning the supernatant was aspirated. Then, one spheroid (100-200 μm) was aspirated into a 0.1-2.0 μl pipette and meticulously embedded in the coating. After incubating the plate for 75 minutes at 36° C., 800 μl serum-free medium was added. When spheroids started migrating (designated day 0) additionally 200 μl of serum-free medium (serving as untreated controls), $^{127}$I-UdR or $^{125}$I-UdR was added resulting in a final concentration of 0.3 μg/ml or 3 kBq/ml of $^{127}$I-UdR or $^{125}$I-UdR, respectively. Images were obtained daily from day 0 to day 5 using a Leica DM IRB inverted phase-contrast microscope, a Leica DFC300FX camera, and the Leica Application Suite version 2.6.0 RI computer software. The radius of the spheroids was determined (http://imagej.nih.gov/ij/) and the migration speed/day was calculated.

Animal Model

All animal procedures were conducted in accordance with the obtained approval from the national Animal Experiments Inspectorate (permission J. Nr. 2008/561-1572). Male athymic nude rats (n=24) aged six weeks (Hsd:RH-Foxnl mu, Harlan laboratories) were anaesthetized subcutaneously (mixture of Hypnorm and Midazolam) and placed in a small animal stereotaxic instrument (Model 900, David Kopf Instruments). Through a midline scalp incision, the bregma was exposed, and one mm anteriorly and two mm laterally to this a burr hole was made. A blunt cannula (Hamilton 7102 syringe) was then advanced to a depth of 3.5 mm (right striatum), and a 2 μl cell suspension of 300,000 T87 single cells in Hank's Balanced Salt Solution (Gibco) supplemented with 0.9% glucose (SAD 500 mg/ml) was slowly injected. After removal of the cannula, the skin was closed with VICRYL 5.0 (Ethicon) disrupted sutures. Two weeks after tumor-cell inoculation, a SMP-200 iPRECIO® Micro Infusion Pump (Data Sciences International) was implanted subcutaneously, since preliminary experiments had shown establishment of tumors at this time point. Infusion protocols (instant mode, constant flow mode and 5 μl/hour infusion rate) were downloaded, and the pumps were conditioned according to Low Flow Infusion Standard Operational Procedure. Rats were anaesthetized and fixated as described above. The midline incision was re-incised and the burr hole was identified. A 4 mm pump connector cannula (PlasticsOne model 328OPM/PK/Spc) was then connected to the pump catheter and implanted (according to the manufactures Technical Note 6) with the tip of the cannula in the center of the bulk tumor. Pumps were loaded with isotone saline (n=8, group I) or 0.1 mM MTX (Sigma-Aldrich) (n=16, group II and III). Finally, the skin was closed with VICRYL 5.0 disrupted sutures. As one of the rats with an MTX loaded pump never woke up after surgery it was censored from the study. Two days later the 23 rats were anaesthetized using isoflurane, and residual saline or MTX was extracted from the pump reservoirs according to the manufacturer's instructions. The reservoirs were refilled with 960 μl of 0.3 μg/m $^{127}$I-UdR (n=8, group I) or twice with the $^{125}$I-UdR activity (n=15, group II and III), enabling 8 days of continuous infusion and a cumulated infused $^{125}$I-UdR activity of 83±7 MBq. Initiated on the same day, 8 of these rats (group III) had a daily IP injection of 200 mg/m² TMZ (Sigma-Aldrich) dissolved in 10% DMSO (Sigma-Aldrich) v/v 0.9% NaCl for five consecutive days.

Rats were fed ad libitum and to block the thyroid gland, KI (Sigma-Aldrich) was added to the drinking water (1 mg/ml) from the day of pump implantation and the following 14 days. At the end of the observation period (180 days after completion of treatment) or once animals reached the pre-determined humane endpoints (neurological deficits or >20% weight-loss) they were anaesthetized by isoflurane and euthanized by intravenous pentobarbital injection.

Distribution Evaluation by SPECT/CT

The intracranial distribution of infused $^{125}$I-UdR was measured at the last day of infusion using a Siemens Inveon Small Animal PET/SPECT/CT scanner. The animals were anesthetized using isoflurane and subsequently SPECT scanned for approximately 42 min using 1.8 mm pinhole collimators (3×1.8 RWB collimators) with 30 projections in 180 degrees rotation. The images were reconstructed using the ordered subset expectation maximization in three dimensions algorithm. In one of the animals a low-dose CT scan was performed in combination with the SPECT scan to visualize the surrounding cranium.

Response Evaluation by PET

For tumor response evaluation, the animals were PET scanned biweekly in the initial phase and later every third week using the Inveon PET scanner. Briefly, the animals were anesthetized using isoflurane and injected via the tail vein with 50 MBq [$^{11}$C]MeAIB, a metabolically stable alanine analogue targeting the amino-acid transport system A. We have previously validated [$^{11}$C]MeAIB for GBM imaging in the same orthotopic model as used in the current study (Dam J H, Halle B, Thisgaard H, Hvidsten S, Kristensen B W, Nagren K. Fully automated radiosynthesis and formulation of C-11 MeAIB applied for in vivo imaging of glioblastoma. Journal of Labelled Compounds & Radiopharmaceuticals. 2013; 56:S112). After the tracer injection pairs of animals were placed head-to-head in the scanner and at 40 min. post injection a 14 min. static scan was performed. The acquired data were reconstructed using the ordered subset expectation maximization in two dimensions algorithm without scatter and attenuation correction in the Inveon Acquisition Workplace software module (Siemens).

Blood Sampling

Blood samples were taken 3 weeks pre-treatment, 3, 5, 13 and 26 weeks post-treatment to evaluate serological signs of potential toxicity. Due to limitations in blood collection volume rats were divided in two groups; one group for thyroid evaluation and one group for hepatic, renal and bone marrow evaluation.

In general, rats were anaesthetized with isoflurane and blood samples were collected via a tail vein catheter. Thyroid function was evaluated using total T3 and T4 ELISA kits (Nordic Biosite) on plasma samples. Plasma levels of ALT, creatinine and BUN were analyzed on a Cobas Mira Plus (Roche) analyzer. Whole blood levels of potassium and sodium were analyzed on a GEM Premier 3000 analyzer (Instrumentation Laboratory). Hb, WBC and platelet counts were determined in whole blood using a scil Vet ABC Hematology Analyzer and the rat species-specific smart card (scil animal care company). All analyses were carried out in accordance with the manufacturer's instructions.

Histology

Brain, thyroid gland, liver and kidneys were removed post-mortem and fixed in 4% formaldehyde. After fixation, brains were divided in one mm thick coronal sections using a rat brain matrix (PlaticsOne) followed by paraffin embedment. Thyroid gland, liver and kidneys were paraffin embedded as well. Three µm sections were cut and all sections were stained with HE for morphological evaluation. To evaluate the human-derived brain tumors, brain sections were immunohistochemically stained with an antibody targeting human vimentin (Nordic Biosite, 1+200) as described by Aaberg-Jessen et al. (Aaberg-Jessen C, Norregaard A, Christensen K, Pedersen C B, Andersen C, Kristensen B W. Invasion of primary glioma- and cell line-derived spheroids implanted into corticostriatal slice cultures. Int J Clin Exp Pathol. 2013; 6:546-60). Additionally, kidney sections were periodic acid-Schiff (PAS) and liver PAS-diastase stained to complement the morphological evaluation.

Statistical Analysis

In vitro and blood sample data were analyzed with unpaired, two-tailed Student's t-tests or two-way ANOVA with Bonferroni correction in GraphPad Prism. The Kaplan-Meier-survival data was analyzed using the log-rank (Mantel-Cox) test. A p-value of <0.05 was considered statistically significant.

Results

Decreased Cell Viability and Spheroid Migration In Vitro

In vitro, the effects of $^{125}$I-UdR were tested on two GSCs (T78 & T87). Cell viability was evaluated using a CellTiter Blue assay. As seen in FIG. 2A, cell survival was significantly decreased (p<0.0001) in both T78 & T87 GSCs for most of the $^{125}$I-UdR activity concentrations used, when compared to untreated controls. The effects of $^{125}$I-UdR compared to the chemically identical but, nonradioactive, $^{127}$I-UdR were also highly significant (p<0.0001) for activity concentrations ≥100 Bq/ml.

Further, to test the anti-migratory effect of $^{125}$I-UdR a 2D migration assay based on migration of spheroids on a coating of reduced growth factor basement membrane extracts was applied. As opposed to many other migration assays, it does not rely on serum-based chemo-attraction and may, therefore, imitate the in vivo migration better. As illustrated (FIG. 2B), spheroid migration was significantly reduced by $^{125}$I-UdR in T78 (FIG. 2C) and T87 (FIG. 2D) GSCs from day three, compared to $^{127}$I-UdR treated spheroids serving as control.

$^{125}$I-UdR Intracerebral Distribution

Delivery of the AEE compound to all cancer cells in vivo is important for efficient tumor eradication due to the short range of the emitted Auger-electrons. By constant intratumoral CED of $^{125}$I-UdR for 8 days in orthotopic GBM-bearing rats (evolved from the T87 GSC), a high concentration of $^{125}$I was found in the tumor region determined by combined Single-Photon Emission Tomography (SPECT) and Computed Tomography (CT) as seen in FIG. 3. Additionally, a small fraction of the $^{125}$I could be seen in the contralateral hemisphere and in the posterior part of the brain, allowing for irradiation of possible distantly located migrating GBM cells.

Significant Antitumor Response and Survival Rate In Vivo

To test the in vivo anti-tumor efficacy of the AEE therapy, 24 orthotopic xenografted GBM-bearing nude rats (evolved from the T87 GSC) were treated with: I)$^{127}$I-UdR by CED, II) neoadjuvant MTX+$^{125}$I-UdR by CED, or III) neoadjuvant MTX+$^{125}$I-UdR by CED+concomitant systemic TMZ as outlined in FIG. 4. Tumors rapidly progressed in all animals in group I, as determined by [$^{11}$C]methylaminoisobutyric acid ([$^{11}$C]MeAIB) Positron Emission Tomography (PET, FIG. 5A). Tumor progression in group II was strongly delayed and only three out of seven animals (FIG. 5B, C) in this group developed a PET-detectable tumor during the 180 days observation period. The time from therapy initiation to the first PET-based tumor detection in group II was 91 days compared to 21 days in group I. None of the animals in group III developed a PET-detectable tumor (FIG. 5D, E) during the 180 days observation period.

The survival benefit of both neoadjuvant MTX+$^{125}$I-UdR as stand-alone therapy (group II) and neoadjuvant MTX+$^{125}$I-UdR with concomitant TMZ (group III) was highly significant (p<0.001 and p<0.0001, respectively) compared with $^{127}$I-UdR therapy (group I) (FIG. 6). Four animals (4/7, 57%) survived the entire observation period in group II and all animals (8/8, 100%) survived in group III. In group I, no animals (0/8) survived longer than 23 days after initiation of treatment due to massive tumor burden.

Post-mortem histology of the brains revealed that all animals in the group I had very large tumors (FIG. 5A) explaining their short survival. The three animals in group II, not surviving the entire observation period, had large tumors as well (FIG. 5B). The remaining animals in this group had an empty tumor-bed (the tissue surrounding the original bulk tumor) with a few GBM cells located in the ipsilateral hemisphere (FIG. 5C). No distant migratory cells could be identified. In group III, five animals had the same histological appearance as just described (FIG. 5D) whereas no vimentin positive GBM cells could be detected in brains of the remaining three animals (FIG. 5E).

No Signs of Dose-Limiting Adverse Effects

The administration of MTX and $^{125}$IUdR by CED directly into the brain parenchyma as well as intraperitoneal (IP) administration of TMZ could potentially give rise to local and/or systemic adverse effects. To evaluate this, blood samples were examined and post-mortem histological analyses performed.

In general, no animals presented with neurological deficits or signs of discomfort indicating brain-related adverse effects due to the infused drugs or the CED procedure itself. All animals reaching the human endpoint of >20% weight-loss had large tumors explaining their terminal weight-loss. The non-tumor infiltrated brain parenchyma was examined using hematoxylin and eosin (HE) stainings of brain sections from all three treatment groups. Overall, the vast majority of neurons had a normal morphology and no astrogliosis was observed. Focal presence of dark neurons in the neocortex (FIG. 7A, C) and the CA3 region of the hippocampus (FIG. 7B, D) were observed in all three groups, which may suggest mild neuronal damage. In the neocortex it was observed in 7/8 (88%) animals in group I, in 6/7 (86%) animals in group II and 6/8 (75%) animals in group III. In the hippocampus it was observed in 4/8 (50%) animals in group I, 6/7 (86%) of animals in group II and in 5/8 (63%) of animals in group III.

Thyroid gland function was evaluated by measurements of total T3 (FIG. 7E) and T4 (FIG. 7F) in plasma. Animals in all three groups had diminished levels post-treatment, but the drop seemed to stabilize from 13 to 26 weeks post-treatment. Histologically, animals in group I presented with normofollicular architecture (FIG. 7G) whereas animals in group II and III presented with microfollicular architecture and colloids with scalloped margins (FIG. 7H), indicative of stimulated and active glands.

Hepatic function was evaluated by measurements of alanine aminotransferase (ALT) and blood urea nitrogen (BUN) levels in plasma. No increase in ALT level (FIG. 7I) was observed in any of the three groups. BUN levels, which encompass both hepatic (production) and renal (excretion) functions, increased after treatment start, but returned to baseline at 26 weeks (FIG. 7J). In all three groups the liver architecture was normal (FIG. 7K-L). There were no signs of hepatocyte necrosis, haemorrhage or inflammation in group I and II. In group III, receiving concomitant TMZ, a few cases of slight portal tract oedema were observed and focally a few necrotic hepatocytes were present (FIG. 7L).

Renal function was assessed by plasma creatinine and whole blood potassium and sodium levels and to some degree plasma BUN levels (as described above). In all three groups, creatinine initially increased (FIG. 7M), whereas potassium decreased after treatment start although statistically non-significant (FIG. 7N). Sodium remained stable throughout the study (FIG. 7O). In all three groups the kidneys appeared histologically normal without any signs of tubular or glomerular damage or interstitial fibrosis (FIG. 7P).

Bone marrow function was assessed by hemoglobin (Hb) level (FIG. 7Q), white blood cell (WBC) (FIG. 7R) and platelet counts (FIG. 7S) measured in whole blood. No signs of bone marrow suppression were observed.

Discussion

Figure 2:
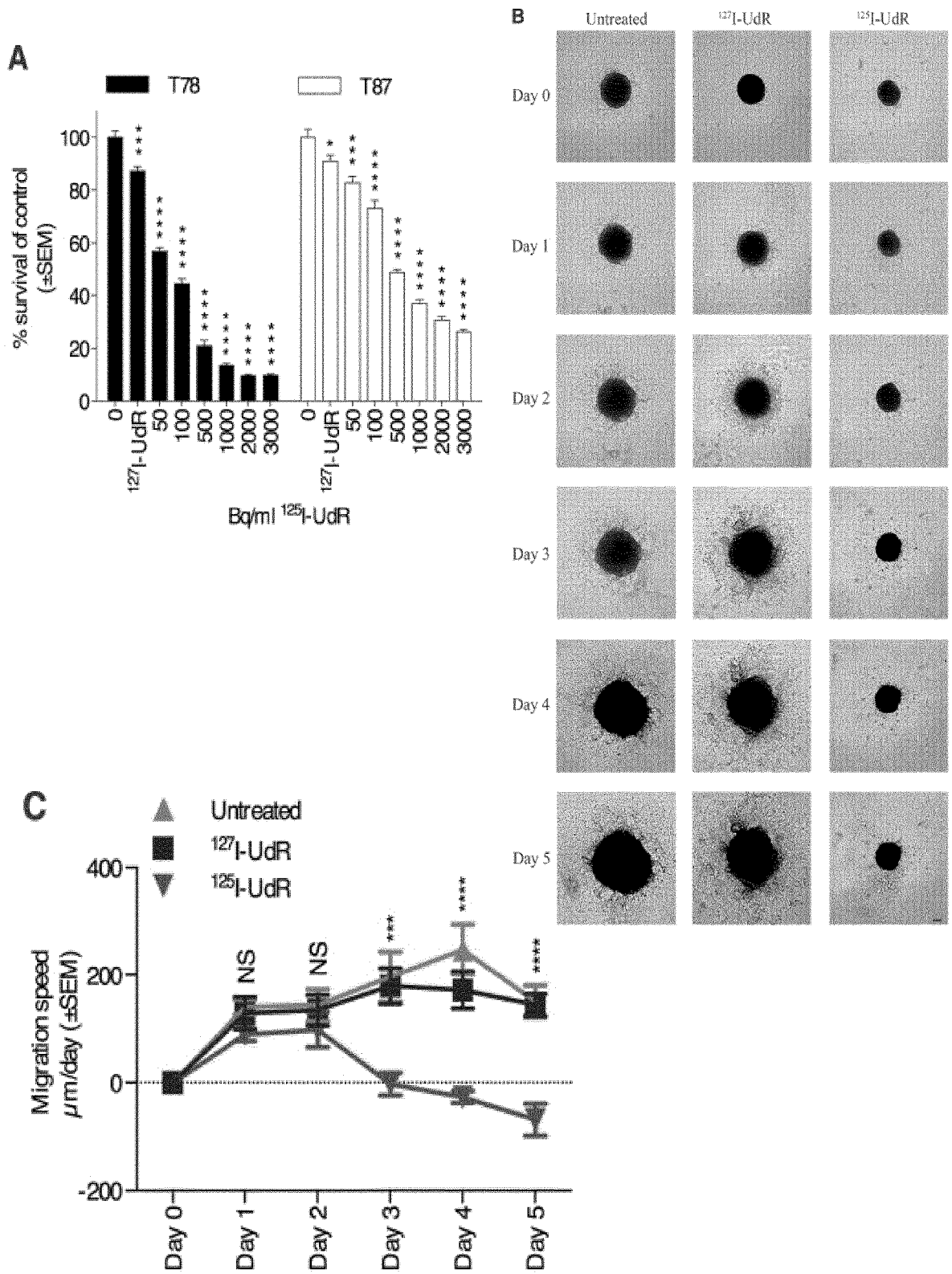
FIG. 2: $^{125}$I-UdR inhibited cell proliferation and spheroid migration. (A) CellTiter-Blue assay showed significant and decreasing cell proliferation when exposing both T78 and T87 glioblastoma (GBM) cells to increasing activity concentrations of $^{125}$I-UdR compared to no treatment or exposure to $^{127}$I-UdR (non-radioactive I-UdR analogue). (B) T87 spheroid migration assay. Migration was unaffected by $^{127}$I-UdR compared to untreated controls, whereas $^{125}$I-UdR clearly inhibited the migratory process. In addition, $^{125}$I-UdR exposed spheroids were not able to expand in size as opposed to untreated or $^{127}$I-UdR exposed spheroids. Scale bar, 100 µm. (C) Graph depicting the mean migration distance per day in T87 spheroids (minimum of 5 spheroids/group) when left untreated, exposed to $^{127}$I-UdR or $^{125}$I-

The very aggressive and infiltrating nature of human glioblastomas warrant for more effective therapeutic strategies. According to the present invention, the use of MTX and the DNA-incorporating AEE compound $^{125}$I-UdR alone or in combination with TMZ effectively eradicate GBM cells including the treatment resistant cancer stem cells via free-radical independent, direct ionization of the DNA molecules. As can be seen in FIG. 2, viability (FIG. 2A) and migration (FIG. 2B-D) were significantly reduced in vitro in the cancer stem cell-enriched GSCs using very low activity concentrations of only $^{125}$I-UdR. This illustrates the therapeutic potential of DNA-incorporated AEEs, which has been well documented in many cell lines. $^{125}$I decays via electron capture accompanied by a high degree of internal conversion, which results in nearly two Auger-electron cascades with on average approximately 20 electrons per decay. This gives rise to a very high radiation dose close to the decay site and high-LET values approaching those observed with α-particles. The complex DSBs created by these Auger electron cascades are very difficult for the cells to repair leading to cell death or loss of proliferative capacity.

In the in vivo study, the infused $^{125}$I-UdR activity concentration was approximately 4-6 orders of magnitude higher than in the in vitro studies. The high concentration was chosen to ensure that distantly located migratory GBM cells were exposed to $^{125}$I-UdR. Moreover, $^{125}$I-UdR was delivered by CED, relying on a pressure-driven bulk flow created by a small pressure gradient from a mechanical pump, to increase the regional distribution compared to simple passive diffusion. This was confirmed by SPECT/CT, which showed that the $^{125}$I-UdR was distributed far away from the catheter tip (FIG. 3). As expected, the SPECT/CT showed a decline in $^{125}$I activity concentration in the contralateral hemisphere and the caudal part of the brain compared to the isocenter of delivery. For that reason, more than one catheter has been applied in the majority of clinical trials that have relied on CED. This is technically difficult in small animals opposed to a full-sized human brain where it would be preferred to obtain a reliable and widespread MTX+$^{125}$I-UdR intracerebral distribution.

The explanation for the incredible therapeutic response in the current study, utilizing animals with established tumors, is probably multifaceted. A very high amount of cumulated activity was infused (approximately 80 MBq), a high infusion rate was applied and a prolonged infusion of 8 days. This results in a higher and a wider intracerebral activity distribution allowing eradication of both bulk tumor and distantly migrated GBM cells and thereby a better antitumor effect. The prolonged infusion increases the probability that all tumor cells will undergo DNA synthesis during the infusion period, and thus, incorporate $^{125}$I-UdR. Finally, neoadjuvant MTX was applied, which is believed to increase the percentage of cells undergoing DNA replication and, simultaneously, to increase the DNA-incorporation of $^{125}$I by thymidylate synthetase inhibition. In a recent study, using the syngeneic C6 glioma model (Lehnert S, Li; Y, Bump E, Riddoch B, Chenite A, Shive M. 125I-Iododeoxyuridine for the Treatment of a Brain Tumor Model: Selection of Conditions for Optimal Effectiveness. Open Nuclear Medicine Journal 2011; 3:19-24), neoadjuvant MTX was also used but in a local implant allowing only simple passive diffusion. The implant contained $^{127}$I-UdR, i.e., 7.4 MBq $^{125}$I-UdR or MTX+7.4 MBq $^{125}$I-UdR. No $^{127}$I-UdR treated animal survived the entire observation period of 180 days, whereas 20% of the $^{125}$I-UdR and 40% of the $^{125}$I-UdR+MTX treated animals did (with median survivals of 20, 35 and 35 days, respectively). In the present study, 57% in group II became long-term survivors, and the addition of TMZ increased this to 100% in group III (FIG. 6). This emphasizes the importance of not only local but also regional intracerebral distribution of high activity concentrations of MTX+$^{125}$I-UdR, which is accomplishable by CED as opposed to local implant techniques. Additionally, the pronounced effect, observed in group III of targeting the tumor cell DNA, using two drugs ($^{125}$I-UdR and TMZ) with different DNA targeting mechanisms, becomes very evident.

A significant anti-tumor effect of MTX itself was not anticipated or likely in the present study. The purpose of the neoadjuvant MTX was solely to increase the incorporation of $^{125}$I-UdR in the tumor cells. Using a human-derived model of meningeal carcinomatosis (induced by intrathecal (IT) injection of TE-671 human rhabdomyosarcoma cells), approximately the same amount of activity as used in the present study has been injected IT as a simple bolus in combination with IT infusion of MTX. Using the median time to onset of paralysis as endpoint, a significant effect was observed with $^{125}$I-UdR alone and when combined with MTX a further increase was observed, though no long-term survivors were seen. The authors later confirmed this synergistic effect. MTX alone had no significant effect.

The profound therapeutic response observed in the two $^{125}$I-UdR treated groups (FIG. 6) in the current study were confirmed by immunohistochemical vimentin staining as no residual bulk tumors were left (FIG. 5C-E). However, in 7/7 (100%) rats in group II and 5/8 (63%) rats in group III, a few tumor cells were found near the original tumor-bed (FIG. 5C, D) 180 days after treatment start. These cells could represent silent cancer stem cells that survived the treatment. Alternatively, the remaining cells may represent non-clonogenic cells that have lost their ability to divide and, thus, from a radiobiological point of view could be regarded as "dead" cells, not able to repopulate the tumor.

The effect of monotherapy with systemic TMZ was not tested in the present study. However, in a study from 2010 (Yokosawa M, Sonoda Y, Sugiyama S, Saito R, Yamashita Y, Nishihara M, et al. Convection-enhanced delivery of a synthetic retinoid Am80, loaded into polymeric micelles, prolongs the survival of rats bearing intracranial glioblastoma xenografts. Tohoku J Exp Med. 2010; 221:257-64), orthotopic xenografted U87MG-bearing nude rats were treated with the exact same TMZ dose-regimen as in our study. This resulted in a 2.9-fold increase in maximum survival, but no animal became a long-term survivors. Extrapolating their data to our findings, this would only result in a maximum survival of 66 days. Therefore, it seems unlikely that monotherapy with TMZ would have induced the same dramatic survival benefits as observed in the current study.

In thius example, no animals showed objective signs of neurotoxicity. Post-mortem histological HE examination of the brains focally showed some dark neurons in the cortex and hippocampus in some of the animals in all three groups (FIG. 7A-D). This may indicate mild focal neuronal damage, but as it was found in all three groups, no relationship with the MTX, $^{125}$I-UdR or TMZ treatment seems likely. As the CED procedure itself has been reported only to induce minimal necrosis and gliosis limited to the region immediately surrounding the cannula track, it is most likely that the dark neurons originate from spatula-pressure applied during post-mortem brain excision.

$^{125}$I-UdR entering the systemic circulation has a short biological half-life of only approximately five minutes due to rapid catabolization and dehalogenation resulting in $^{125}$I-uracil and free $^{125}$I$^-$. None of these compounds are incorporated into the genomic DNA during cell division in normal tissue (as the $^{125}$I-UdR), which is required for high-LET-like radiotoxic effects and hence, no severe adverse effects were anticipated. In line with this, blood parameters evaluating the bone marrow, harboring some of the most rapidly dividing cells in the body, remained unaffected (FIG. 7Q-S). The kidneys are another important potential dose-limiting organ, because of their excretion of free $^{125}$I. They responded with an increase in creatinine, which remained (FIG. 7M), but apparently with little functional impact judged by the course of BUN (FIG. 7I) and the excretion of potassium and sodium, and the lack of histological changes (FIG. 7N-P). To prevent uptake of free $^{125}$I$^-$ in the thyroid gland the drinking water was supplemented with potassium iodine (KI). Histologically, animals from group II and III had a microfollicular thyroid architecture and colloids with scalloped margins (FIG. 7H), which are signs of stimulated and active glands. Probably, this indicates that the thyroid blocking was not complete, leading to some uptake of free $^{125}$I$^-$ resulting in a certain radiation dose to the gland. Since total T3 and T4 trends were similar in all three groups (FIG. 7E, F) during the study, the impact was not functionally significant.

Finally, signs of hepatotoxicity were assessed. In group III, a few animals presented with slight portal tract oedema and focally a few necrotic hepatocytes were present (FIG. 7L). In the remaining two groups histology was inconspicuous (FIG. 7K). As opposed to MTX, which is known to be highly hepatotoxic, TMZ has only been reported casuistically to induce liver injury (toxic hepatitis). As such, the histological changes observed in group III were only very subtle. In addition, blood samples in all three groups showed no signs of sustained toxic effects (FIG. 7I, J) and, therefore, we regard the treatments non-hepatotoxic. Summarized, CED of MTX+$^{125}$I-UdR in combination with concomitant systemic TMZ proved safe without signs of dose-limiting adverse effects.

In conclusion, the multidrug approach including CED of MTX and the AEE-compound $^{125}$I-UdR in combination with systemic TMZ was found to be safe and extremely efficient in the orthotopic xenograft GBM model, leading to 100% survival. This demonstrates that this AEE-based therapeutic strategy could improve the treatment of patients suffering from the presently incurable GBMs.

Items

The present invention specifically comprises embodiments according to items I-1 to I-37 as identified herein below:

I-1. A radioactive agent characterized by a short-range cytotoxic ionizing radiation for use in treating or ameliorating a high-grade glioma (WHO grade III-IV), wherein said agent is administered by intracerebral convection-enhanced delivery.

I-2. The radioactive agent of item I-1, which further comprises at least one further therapeutic agent, which is administered by convection-enhanced delivery.

I-3. The radioactive agent according to item I-2, wherein said further therapeutic agent is an adjuvant or neoadjuvant.

I-4. The radioactive agent according to item I-2, wherein said further therapeutic agent is a thymidylate synthetase inhibitor, such as methotrexate, or 5-fluoro-2'-deoxyuridine (F-UdR), or non-radioactive 5-iodo-2'-deoxyuridine (1-UdR).

I-5. The radioactive agent according to any of items I-2 to I-4, wherein said further therapeutic agent is administered before, simultaneously or after the administration of said radioactive agent.

I-6. The radioactive agent according to any of the preceding items, wherein said high-grade glioma is selected from anaplastic astrocytomas (WHO grade III) and glioblastoma multiforme (WHO grade IV).

I-7. The radioactive agent according to any of the preceding items, wherein said radioactive agent comprises an Auger electron emitting radioisotope.

I-8. The radioactive agent according to item I-7, wherein said Auger electron emitting radioisotope is 77Br, 80mBr, 123I, 124I, 125I or 126I.

I-9. The radioactive agent according to any of the preceding items, wherein said radioactive agent comprises the α-emitter 211At or the β-emitter 131I.

I-10. The radioactive agent according to any of the preceding items, wherein the radioactive agent comprises an Auger-electron emitting radionucleoside or an analog or a prodrug thereof.

I-11. The radioactive agent according to any of the preceding items, wherein said agent is 5-[125I]-iodo-2'-deoxyuridine (125I-UdR).

I-12. The radioactive agent according to any of the preceding items, wherein said radioactive agent and optionally said further therapeutic agent is administered at an infusion rate of 0.1-5 ml/hour, preferably about 0.5 ml/hour.

I-13. The radioactive agent according to any of the preceding items, wherein said radioactive agent and optionally said further therapeutic agent is administered in I-20 fractions, preferably 1-5 fractions.

I-14. The radioactive agent according to item I-13, wherein each fraction comprises 1 kBq to 50 GBq of said radioactive agent and optionally 1 microg to 25 mg of said further therapeutic agent (such as MTX or F-Udr).

I-15. The radioactive agent according to any of the preceding items, wherein a composition comprising 1 kBq to 50 GBq, such as 0.1-3.7 GBq, preferably 0.1-2 GBq, radioactive agent is administered.

I-16. The radioactive agent according to any of the preceding items, wherein a composition comprising 0.01 microgram to 5 mg/mL, preferably 2.5 mg/mL or 2.5 microg/mL of said further therapeutic agent is administered.

I-17. The radioactive agent according to any of the preceding items, which further comprises at least one additional chemotherapeutic agent suitable for treating or ameliorating a high-grade glioma, such as glioblastoma multiforme, wherein said additional agent is administered by systemic administration.

I-18. The radioactive agent and at least one additional chemotherapeutic agent according to item I-17, wherein said additional chemotherapeutic agent is an alkylating agent, a topoisomerase inhibitor, such as Irinotecan (type 1 topoisomerase) or Etoposide (type 2 topoisomerase), or a vascular endothelial growth factor (VEGF) inhibitor, such as Bevazizumab.

I-19. The radioactive agent and at least one additional chemotherapeutic agent according to item I-17, wherein said additional chemotherapeutic agent is selected from Nitrogen mustards, such as Cyclophosphamide, Mechlorethamine or mustine (HN2) (trade name Mustargen), Uramustine or uracil mustard, Melphalan, Chlorambucil, Ifosfamide and Bendamustine, or is selected from Nitrosoureas, such as Carmustine, Lomustine and Streptozocin; or is selected from Alkyl sulfonate, such as Busulfan, or is Thiotepa or an analogue thereof, or is selected from Platinum-based chemotherapeutic agents, such as Cisplatin, Carboplatin, Nedaplatin, Oxaliplatin, Satraplatin, and Triplatin tetranitrate, or is selected from procarbazine, altretamine or tetrazines, such as dacarbazine, mitozolomide and temozolomide, or is selected from topoisomerase inhibitors such as amsacrine, etoposide, etoposide phosphate, teniposide, doxorubicin, irinotecan, topotecan, exatecan, lurtotecan, or is selected from VEGF inhibitors such as bevacizumab and ranibizumab.

I-20. The radioactive agent and at least one additional chemotherapeutic agent according to item I-17, wherein said additional chemotherapeutic agent is temozolomide (TMZ).

I-21. A method of treating or ameliorating a high-grade glioma in a patient comprising intracerebral administering of a radioactive agent characterized by a short-range cytotoxic ionizing radiation by convection-enhanced delivery to a person in need thereof.

I-22. The method according to item I-21, which further comprises administering at least one further therapeutic agent by intracerebral convection-enhanced delivery.

I-23. The method according to any of the preceding items I-21 to I-22, wherein said further therapeutic agent is an adjuvant or neoadjuvant.

I-24. The method according to any of the preceding items I-21 to I-23, wherein said high-grade glioma is selected from anaplastic astrocytomas (WHO grade III) and glioblastoma multiforme (WHO grade IV).

I-25. The method according to any of the preceding items I-21 to I-24, wherein said radioactive agent comprises an Auger electron emitting radioisotope.

I-26. The method according to any of the preceding items I-21 to I-25, wherein said radioactive agent is 5-[125I]-iodo-2'-deoxyuridine (125I-UdR).

I-27. The method according to any of the preceding items I-21 to I-26, wherein said radioactive agent and optionally said further therapeutic agent is administered at an infusion rate of 0.1-5 ml/hour, preferably about 0.5 ml/hour.

I-28. The method according to any of the preceding items I-21 to I-27, wherein said radioactive agent and optionally said further therapeutic agent is administered in I-20 fractions, preferably 1-5 fractions.

I-29. The method according to any of the preceding items I-21 to I-28, wherein each fraction comprises 1 kBq to 50 GBq of said radioactive agent and optionally 1 microg to 25 mg of said further therapeutic agent (such as MTX or F-Udr).

I-30. The method according to any of the preceding items I-21 to I-29, wherein a composition comprising 1 kBq to 50 GBq, preferably 0.1-3.7 GBq, such as 0.1-2 GBq, radioactive agent is administered.

I-31. The method according to any of the preceding items I-21 to I-30, wherein a composition comprising 1 microg to 25 mg, such as 0.01-5 mg/mL, preferably 2.5 mg/mL of said further therapeutic agent is administered.

I-32. The method according to any of the preceding items I-21 to I-31, which further comprises administering at least one additional chemotherapeutic agent suitable for treating or ameliorating a high-grade glioma, wherein said additional agent is administered by systemic administration.

I-33. The method according to any of the preceding items I-21 to I-32, wherein said additional chemotherapeutic agent is temozolomide (TMZ).

I-34. A kit-of-parts comprising a combined preparation comprising or containing 1) a radioactive agent characterized by a short-range cytotoxic ionizing radiation and 2) at least one further therapeutic agent and/or at least one additional chemotherapeutic agent, for the simultaneous, separate or sequential administration for treating or ameliorating a high-grade glioma.

I-35. The kit-of-parts according to item I-34, wherein said at least one additional therapeutic agent is an adjuvant or a neoadjuvant.

I-36. The kit-of-parts according to item I-34, wherein said at least one additional therapeutic agent is a chemotherapeutic agent suitable for treating or ameliorating a high-grade glioma, such as glioblastoma multiforme, I-37. A radioactive agent characterized by a short-range cytotoxic ionizing radiation for use in the manufacture of a medicament for the treatment or amelioration of a high-grade glioma, wherein said radioactive agent is administered by convection-enhanced delivery.

The present invention also comprises the specific embodiments according to items II-1 to II-15 as identified herein below:

II-1. A radioactive agent characterized by a short-range cytotoxic ionizing radiation for use in treating or ameliorating a high-grade glioma (WHO grade III-IV), wherein said agent is administered by intracerebral convection-enhanced delivery.

II-2. The radioactive agent of item 1, which further comprises at least one further therapeutic agent, which is administered by convection-enhanced delivery.

II-3. The radioactive agent according to item II-2, wherein said further therapeutic agent is an adjuvant or neoadjuvant.

II-4. The radioactive agent according to item II-2, wherein said further therapeutic agent is a thymidylate synthetase inhibitor, such as methotrexate, or 5-fluoro-2'-deoxyuridine (F-UdR), or non-radioactive 5-iodo-2'-deoxyuridine (1-UdR).

II-5. The radioactive agent according to any of the preceding items, wherein said high-grade glioma is selected from anaplastic astrocytomas (WHO grade III) and glioblastoma multiforme (WHO grade IV).

II-6. The radioactive agent according to any of the preceding items, wherein said radioactive agent comprises an Auger electron emitting radioisotope selected from 77Br, 80mBr, 123I, 124I, 125I or 126I or the α-emitter 211At or the β-emitter 131I.

II-7. The radioactive agent according to any of the preceding items, wherein said agent is 5-[125I]-iodo-2'-deoxyuridine (125I-UdR).

II-8. The radioactive agent according to any of the preceding items, wherein said radioactive agent and optionally said further therapeutic agent is administered at an infusion rate of 0.1-5 ml/hour, preferably about 0.5 ml/hour.

II-9. The radioactive agent according to any of the preceding items, wherein said radioactive agent and optionally said further therapeutic agent is administered in I-20 fractions, preferably 1-5 fractions.

II-10. The radioactive agent according to item II-9, wherein each fraction comprises 1 kBq to 50 GBq of said radioactive agent and optionally 1 microg to 25 mg, such as I-25 mg of said further therapeutic agent (such as MTX or F-Udr).

II-11. The radioactive agent according to any of the preceding items, which further comprises at least one additional chemotherapeutic agent suitable for treating or ameliorating a high-grade glioma, such as glioblastoma multiforme, wherein said additional agent is administered by systemic administration.

II-12. The radioactive agent and at least one additional chemotherapeutic agent according to item II-11, wherein said additional chemotherapeutic agent is temozolomide (TMZ).

II-13. A kit-of-parts comprising a combined preparation comprising or containing 1) a radioactive agent characterized by a short-range cytotoxic ionizing radiation and 2) at least one further therapeutic agent and/or at least one additional chemotherapeutic agent, for the simultaneous, separate or sequential administration for treating or ameliorating a high-grade glioma.

II-14. The kit-of-parts according to item II-13, wherein said at least one additional therapeutic agent is an adjuvant or a neoadjuvant.

II-15. The kit-of-parts according to item II-13, wherein said at least one additional therapeutic agent is a chemotherapeutic agent suitable for treating or ameliorating a high-grade glioma, such as glioblastoma multiforme,

The invention claimed is:

1. A method of treating or ameliorating a high-grade glioma comprising administering:
   a) a radioactive agent comprising an Auger electron emitting radioisotope selected from the group consisting of $^{77}$Br, $^{80m}$Br, $^{125}$I, $^{124}$I, $^{125}$I and $^{126}$I;
   b) a further agent selected from methotrexate and 5-Fluorodeoxyuridine; and
   c) temozolomide to a person in need thereof, wherein said radioactive agent and said further agent are administered by intracerebral convection-enhanced delivery.

2. The method according to claim 1, wherein said temozolomide is administered by systemic administration.

3. The method according to claim 1, wherein said high-grade glioma is selected from anaplastic astrocytoma and glioblastoma multiforme.

4. The method according to claim 1, wherein said radioactive agent is 5-[$^{125}$I]-iodo-2'-deoxyuridine.

5. The method according to claim 1, here in the further agent is methotrexate.

6. The method according to claim 1, wherein the further agent is 5-Fluoro-2'-deoxyuridine.

7. The method according to claim 1, wherein the radioactive agent comprises a halogenated nucleoside analogue or a prodrug thereof.

8. A method of treating or ameliorating a high-grade glioma comprising administering:
   a) 5-[$^{125}$I]-iodo-2'-deoxyuridine,
   b) methotrexate, and
   c) temozolomide,
to a person in need thereof, wherein said 5-[$^{125}$I]-iodo-2'-deoxyuridine and said methotrexate are administered by intracerebral convection-enhanced delivery.

* * * * *

UNITED STATES PATENT AND TRADEMARK OFFICE
CERTIFICATE OF CORRECTION

PATENT NO. : 10,583,210 B2
APPLICATION NO. : 15/320113
DATED : March 10, 2020
INVENTOR(S) : Helge Thisgaard et al.

It is certified that error appears in the above-identified patent and that said Letters Patent is hereby corrected as shown below:

In the Claims

Column 36, Line 36: Replace "$^{125}$I" (first occurrence) with --$^{123}$I--.

Signed and Sealed this
Fourteenth Day of February, 2023

Katherine Kelly Vidal
*Director of the United States Patent and Trademark Office*